(12) United States Patent

Mazzone et al.

(10) Patent No.: US 12,636,470 B2

(45) Date of Patent: May 26, 2026

(54) TISSUE TREATMENT CATHETER HAVING SUPPORTIVE ISOLATION TUBE

(71) Applicant: Otsuka Medical Devices Co., Ltd., Tokyo (JP)

(72) Inventors: James D. Mazzone, San Jose, CA (US); Eric Dailey, San Jose, CA (US); Desmond Cheung, San Jose, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 137 days.

(21) Appl. No.: 18/509,197

(22) Filed: Nov. 14, 2023

(65) Prior Publication Data

US 2024/0157093 A1 May 16, 2024

Related U.S. Application Data

(60) Provisional application No. 63/383,816, filed on Nov. 15, 2022.

(51) Int. Cl.
| | |
|---|---|
| *A61M 25/09* | (2006.01) |
| *A61B 18/14* | (2006.01) |
| *A61B 18/00* | (2006.01) |

(52) U.S. Cl.
CPC ......... *A61M 25/09* (2013.01); *A61B 18/1492* (2013.01); *A61B 2018/00577* (2013.01); *A61M 2025/09008* (2013.01)

(58) Field of Classification Search
CPC ...... A61B 18/1492; A61B 2018/00285; A61B 2018/00375; A61B 2018/00434; A61B 2018/00511; A61B 2018/00577; A61B 2018/00994; A61M 2025/09008; A61M 25/09; A61N 2007/003; A61N 2007/025; A61N 7/02

See application file for complete search history.

(56) References Cited

U.S. PATENT DOCUMENTS

| | | | |
|---|---|---|---|
| 4,554,925 | A | 11/1985 | Young |
| 4,643,186 | A | 2/1987 | Rosen |
| 4,650,466 | A | 3/1987 | Luther |
| 4,709,698 | A | 12/1987 | Johnston et al. |

(Continued)

FOREIGN PATENT DOCUMENTS

| | | |
|---|---|---|
| CN | 105188830 | 12/2015 |
| CN | 105744901 | 7/2016 |

(Continued)

OTHER PUBLICATIONS

Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.

(Continued)

*Primary Examiner* — Mark D Remaly

(74) *Attorney, Agent, or Firm* — Theresa Ann Raymer

(57) ABSTRACT

A tissue treatment catheter includes a catheter shaft having a fluid lumen in fluid communication with an interior of a balloon, and a guidewire lumen. The balloon is mounted on the catheter shaft and contains an ultrasound transducer. An isolation tube extends through the ultrasound transducer and into the guidewire lumen. A proximal tube end of the isolation tube is between a distal shaft end of the catheter shaft and a guidewire port of the catheter shaft. Other embodiments are also described and claimed.

29 Claims, 20 Drawing Sheets

(56) References Cited

U.S. PATENT DOCUMENTS

| | | | |
|---|---|---|---|
| 4,841,977 A | 6/1989 | Griffith et al. |
| 4,983,169 A | 1/1991 | Furukawa |
| 5,000,185 A | 3/1991 | Yock |
| 5,114,423 A | 5/1992 | Kasprzyk |
| 5,368,591 A | 11/1994 | Lennox |
| 5,391,197 A | 2/1995 | Burdette et al. |
| 5,423,811 A | 6/1995 | Imran et al. |
| 5,558,672 A | 9/1996 | Edwards et al. |
| 5,575,788 A | 11/1996 | Baker et al. |
| 5,657,755 A | 8/1997 | Desai |
| 5,685,839 A | 11/1997 | Edwards et al. |
| 5,688,266 A | 11/1997 | Edwards et al. |
| 5,800,482 A | 9/1998 | Pomeranz et al. |
| 6,066,134 A | 5/2000 | Eggers et al. |
| 6,097,985 A | 8/2000 | Kasevich et al. |
| 6,117,101 A | 9/2000 | Diederich et al. |
| 6,254,598 B1 | 7/2001 | Edwards |
| 6,283,989 B1 | 9/2001 | Laufer et al. |
| 6,292,695 B1 | 9/2001 | Webster |
| 6,296,619 B1 | 10/2001 | Brisken et al. |
| 6,383,151 B1 | 5/2002 | Diederich et al. |
| 6,514,249 B1 | 2/2003 | Maguire et al. |
| 6,529,756 B1 | 3/2003 | Phan |
| 6,564,096 B2 | 5/2003 | Mest |
| 6,584,360 B2 | 6/2003 | Francischelli et al. |
| 6,635,054 B2 | 10/2003 | Fjield et al. |
| 6,648,883 B2 | 11/2003 | Francischelli et al. |
| 6,669,655 B1 | 12/2003 | Acker |
| 6,692,490 B1 | 2/2004 | Edwards |
| 6,719,755 B2 | 4/2004 | Sliwa, Jr. et al. |
| 6,763,722 B2 | 7/2004 | Field et al. |
| 6,837,886 B2 | 1/2005 | Collins |
| 6,845,267 B2 | 1/2005 | Harrison et al. |
| 6,954,977 B2 | 10/2005 | Maguire |
| 7,052,695 B2 | 5/2006 | Kalish |
| 7,156,816 B2 | 1/2007 | Schwartz et al. |
| 7,162,303 B2 | 1/2007 | Levin et al. |
| 7,371,231 B2 | 5/2008 | Rioux et al. |
| 7,510,536 B2 | 3/2009 | Foley et al. |
| 7,617,005 B2 | 11/2009 | Demarais et al. |
| 7,621,873 B2 | 11/2009 | Owen et al. |
| 7,653,438 B2 | 1/2010 | Deem et al. |
| 7,717,948 B2 | 5/2010 | Demarais et al. |
| 7,854,733 B2 | 12/2010 | Govari |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,137,274 B2 | 3/2012 | Weng et al. |
| 8,447,414 B2 | 5/2013 | Johnson et al. |
| 8,483,831 B1 | 7/2013 | Hiavka et al. |
| 8,626,300 B2 | 1/2014 | Demarais et al. |
| 8,702,619 B2 | 4/2014 | Wang |
| 8,774,913 B2 | 7/2014 | Demarais et al. |
| 8,790,281 B2 | 7/2014 | Diederich et al. |
| 8,818,514 B2 | 8/2014 | Zarins et al. |
| 8,845,629 B2 | 9/2014 | Demarais et al. |
| 8,932,289 B2 | 1/2015 | Mayse et al. |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 11/2015 | Demarais et al. |
| 9,186,212 B2 | 11/2015 | Nabulovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 7,717,948 C1 | 8/2016 | Demarais et al. |
| 9,427,579 B2 | 8/2016 | Fain et al. |
| 9,439,598 B2 | 9/2016 | Shimada et al. |
| 9,649,064 B2 | 5/2017 | Toth et al. |
| 9,700,372 B2 | 7/2017 | Schaer |
| 9,707,034 B2 | 7/2017 | Schaer |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,350,440 B2 | 7/2019 | Taylor et al. |
| 10,363,359 B2 | 7/2019 | Toth et al. |
| 10,368,775 B2 | 8/2019 | Hettrick et al. |
| 10,368,944 B2 | 8/2019 | Schaer |
| 10,376,310 B2 | 8/2019 | Fain et al. |
| 10,383,685 B2 | 8/2019 | Gross et al. |
| 10,398,332 B2 | 9/2019 | Min et al. |
| 10,456,605 B2 | 10/2019 | Taylor et al. |
| 10,470,684 B2 | 11/2019 | Toth et al. |
| 10,478,249 B2 | 11/2019 | Gross et al. |
| 10,499,937 B2 | 12/2019 | Warnking |
| 10,543,037 B2 | 1/2020 | Shah |
| 10,850,091 B2 | 12/2020 | Zarins et al. |
| 11,801,085 B2 | 10/2023 | Wu et al. |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |
| 2003/0216792 A1 | 11/2003 | Levin |
| 2004/0019349 A1 | 1/2004 | Fuimaono et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0181178 A1 | 9/2004 | Aldrich et al. |
| 2004/0230178 A1 | 11/2004 | Wu |
| 2004/0242999 A1 | 12/2004 | Vitek et al. |
| 2005/0038340 A1 | 2/2005 | Vaezy et al. |
| 2005/0113822 A1 | 5/2005 | Fuimaono et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0261672 A1 | 11/2005 | Deem et al. |
| 2005/0288730 A1 | 12/2005 | Deem |
| 2006/0041277 A1 | 2/2006 | Deem et al. |

(56) References Cited

U.S. PATENT DOCUMENTS

| | | | |
|---|---|---|---|
| 2006/0052695 | A1 | 3/2006 | Adam et al. |
| 2006/0058711 | A1 | 3/2006 | Harhen et al. |
| 2006/0064081 | A1 | 3/2006 | Rosinko |
| 2006/0118127 | A1 | 6/2006 | Chinn |
| 2006/0142827 | A1 | 6/2006 | Willard et al. |
| 2006/0184069 | A1 | 8/2006 | Vaitekunas |
| 2006/0217772 | A1 | 9/2006 | Libbus et al. |
| 2006/0235286 | A1 | 10/2006 | Stone et al. |
| 2007/0060921 | A1 | 3/2007 | Janssen et al. |
| 2007/0072741 | A1 | 3/2007 | Robideau et al. |
| 2007/0106292 | A1 | 5/2007 | Kaplan |
| 2007/0135875 | A1 | 6/2007 | Demarais et al. |
| 2008/0039746 | A1 | 2/2008 | Hissong et al. |
| 2008/0215031 | A1 | 9/2008 | Belfort et al. |
| 2009/0234407 | A1 | 9/2009 | Hastings et al. |
| 2009/0248005 | A1 | 10/2009 | Rusin et al. |
| 2011/0118723 | A1 | 5/2011 | Turner et al. |
| 2011/0125206 | A1 | 5/2011 | Bornzin |
| 2011/0208096 | A1 | 8/2011 | Demarais et al. |
| 2012/0004656 | A1 | 1/2012 | Jackson et al. |
| 2012/0265198 | A1 | 10/2012 | Crow et al. |
| 2012/0296232 | A1 | 11/2012 | Ng |
| 2013/0023897 | A1 | 1/2013 | Wallace |
| 2013/0085489 | A1 | 4/2013 | Fain et al. |
| 2013/0096550 | A1 | 4/2013 | Hill |
| 2013/0116737 | A1 | 5/2013 | Edwards et al. |
| 2013/0123770 | A1 | 5/2013 | Smith |
| 2013/0131743 | A1 | 5/2013 | Yamasaki et al. |
| 2013/0150749 | A1 | 6/2013 | McLean et al. |
| 2013/0165925 | A1 | 6/2013 | Mathur et al. |
| 2013/0172872 | A1 | 7/2013 | Subramaniam |
| 2013/0197555 | A1 | 8/2013 | Schaer |
| 2013/0274614 | A1 | 10/2013 | Shimada et al. |
| 2013/0289369 | A1 | 10/2013 | Margolis |
| 2013/0289682 | A1 | 10/2013 | Barman et al. |
| 2014/0018788 | A1 | 1/2014 | Engelman et al. |
| 2014/0058294 | A1 | 2/2014 | Gross et al. |
| 2014/0257271 | A1 | 9/2014 | Mayse et al. |
| 2014/0274614 | A1 | 9/2014 | Min et al. |
| 2014/0275924 | A1 | 9/2014 | Min et al. |
| 2014/0288551 | A1 | 9/2014 | Bharmi et al. |
| 2014/0288616 | A1 | 9/2014 | Rawat et al. |
| 2014/0303617 | A1 | 10/2014 | Shimada |
| 2015/0289931 | A1 | 10/2015 | Puryear et al. |
| 2016/0000345 | A1 | 1/2016 | Kobayashi et al. |
| 2016/0045121 | A1 | 2/2016 | Akingba et al. |
| 2016/0262777 | A1 | 9/2016 | Stigall et al. |
| 2017/0027460 | A1 | 2/2017 | Shimada et al. |
| 2017/0035310 | A1 | 2/2017 | Shimada et al. |
| 2017/0296264 | A1 | 10/2017 | Wang |
| 2018/0022108 | A1 | 1/2018 | Mori et al. |
| 2018/0042670 | A1 | 2/2018 | Wang et al. |
| 2018/0064359 | A1 | 3/2018 | Pranaitis |
| 2018/0078307 | A1 | 3/2018 | Wang et al. |
| 2018/0185091 | A1 | 7/2018 | Toth et al. |
| 2018/0221087 | A1 | 8/2018 | Puryear et al. |
| 2018/0249958 | A1 | 9/2018 | Toth et al. |
| 2018/0250054 | A1 | 9/2018 | Gross et al. |
| 2018/0280082 | A1 | 10/2018 | Puryear et al. |
| 2018/0289320 | A1 | 10/2018 | Toth et al. |
| 2018/0310991 | A1 | 11/2018 | Pike |
| 2018/0333204 | A1 | 11/2018 | Ng |
| 2019/0046111 | A1 | 2/2019 | Toth et al. |
| 2019/0046264 | A1 | 2/2019 | Toth et al. |
| 2019/0076191 | A1 | 3/2019 | Wang |
| 2019/0110704 | A1 | 4/2019 | Wang |
| 2019/0134396 | A1 | 5/2019 | Toth et al. |
| 2019/0151670 | A1 | 5/2019 | Toth et al. |
| 2019/0183560 | A1 | 6/2019 | Ballakur et al. |
| 2019/0245310 | A1 | 8/2019 | Medina et al. |
| 2019/0307361 | A1 | 10/2019 | Hettrick et al. |
| 2020/0046248 | A1 | 2/2020 | Toth et al. |
| 2020/0077907 | A1 | 3/2020 | Shimada et al. |
| 2022/0304712 | A1 | 9/2022 | Thirumalai et al. |

FOREIGN PATENT DOCUMENTS

| | | |
|---|---|---|
| CN | 106178294 | 12/2016 |
| CN | 111684665 | 9/2020 |
| EP | 1299035 | 4/2003 |
| EP | 1503685 | 2/2005 |
| EP | 1579889 | 9/2005 |
| EP | 2359764 | 8/2011 |
| EP | 2430996 | 3/2012 |
| EP | 2842604 | 3/2015 |
| EP | 2968984 | 1/2016 |
| EP | 2995250 | 3/2016 |
| EP | 3799931 | 4/2021 |
| WO | WO1999/002096 | 1/1999 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO2006/041881 | 4/2006 |
| WO | WO2006/060053 | 6/2006 |
| WO | WO2007/014003 | 2/2007 |

OTHER PUBLICATIONS

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L. et al., "Control of interstitial thermal coagulation: Comparative evaluation of microwave and ultrasound applicators," Medical Physics vol. 28, No. 1, p. 104-117, Jan. 2001.

Dinerman, Jay L. et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A. et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue—A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, p. S2-S11, Oct. 2004.

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

Lafon, C. et al., "Design and Preliminary Results of an Ultrasound Applicator for Interstitial Thermal Coagulation," Ultrasound in Medicine & Biology, vol. 24, No. 1, p. 113-122, 1998.

Lewis, Matthew A. et al., "Thermometry and Ablation Monitoring with Ultrasound," Int. J. Hyperthermia vol. 31, Issue 2, p. 163-181, Mar. 2015.

Liu, Xinmeng et al., "Visualization and mapping of the right phrenic nerve by intracardiac echocardiography during atrial fibrillation ablation," Europace vol. 25, p. 1352-1360, 2023.

Mendelsohn, Farrell O., "Microanatomy of the Renal Sympathetic Nervous System," Endovascular Today, p. 59-62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.

(56)           References Cited

OTHER PUBLICATIONS

Quadri, Syed A. et al., "High-intensity focused ultrasound: past, present, and future in neurosurgery," Neurosurgical Focus, vol. 44, No. 2, p. 1-9, Feb. 2018.

Ross, Anthony B. et al., "Highly directional transurethral ultrasound applicators with rotational control for MRI-guided prostatic thermal therapy," Physics in Medicine & Biology, vol. 49, p. 189-204, Jan. 2004.

Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.

Sanghvi, Kintur et al., "Rationale and design for studies of renal denervation in the absence (Spyral HTN Off-Med) and presence (Spyral HTN On-Med) of antihypertensive medications," American Heart Journal, vol. 180, p. e1-e2. Oct. 2016.

Satou, Shunsuke et al., "Observation of renal sympathetic nerves by intravascular ultrasound," Hypertension Research vol. 42, p. 1092-1094, 2019.

Schmidt, Boris et al., "Balloon Catheters for Pulmonary Vein Isolation," Herz vol. 33, p. 580-584, 2008.

Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.

Stauffer, P.R. et al., "13 Interstitial Heating Technologies," Thermoradiotherapy and Thermochemotherapy, p. 279-320, 1995.

Swanson, David K. et al., "Tissue temperature Feedback Control of Power, The Key to Successful Ablation," Innovations, vol. 6 No. 4, p. 276-282, Jul./Aug. 2011.

Tabei, Makoto et al., "A k-space method for coupled first-order acoustic propagation equations," J. Acoust. Soc. Am., vol. 111, No. 1, pt. 1, p. 53-63, Jan. 2002.

Tzafriri, Abraham R. et al., "Innervation Patterns May Limit Response to Endovascular Renal Denervation," Journal of the American College of Cardiology, vol. 64, No. 11, p. 1079-1087, Sep. 2014.

Umemura, Shin-ichiro, "Focused ultrasound transducer for thermal treatment," International Journal of Hyperthermia, vol. 31, No. 2, p. 216-221, 2015.

Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.

Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

None

Taiwanese Office Action from Taiwanese Patent Application No. 112144098, mailed Oct. 8, 2024, 19 pages.

International Search Report and Written Opinion mailed May 8, 2024, received in International Application No. PCT/IB2023/061513, 23 pages.

Accornero, Neri et al., "Selective Activation of Peripheral Nerve Fibre Groups of Different Diameter By Triangular Shaped Stimulus Pulses", J. Physiol. (1977), 273, 539-560, 22 Q9S.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

American Heart Association—Pulmonary Hypertension: High Blood Pressure in the Heart-to-Lung System, (last reviewed Oct. 31, 2016).

Appeal Brief of Patent Owner from Reexamination 95-002, 110.

Aytac et al., "Correlation Between the Diameter of the Main Renal Artery and the Presence of an Accessory Renal Artery", J Ultrasound Med 22:433-439, 2003.

Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).

Bailey, M. R. et al., Physical Mechanisms of the Therapeutic Effect of Ultrasound (A Review), Acoustical Physics, vol. 49, No. 4, 2003, pp. 369-388.

Bengel et al., Serial Assessment of Sympathetic Reinnervation After Orthotopic Heart Transplantation; A Longitudinal Study Using PET and C-11 Hydroxyephedrine, Circulation. 1999;99: 1866-1871.

Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.

Bhatt, D. L. et al., A Controlled Trial of Renal Denervation for Resistant Hypertension, New England J. Med., 370:1393-1401 (2014).

Bhatt, Deepak L. et al., Long-term outcomes after catheter-based renal artery denervation for resistant hypertension: final follow-up of the randomised Symplicity HTN-3 Trial, 400 Lancet 1405 (2022).

Billard, B. E. et al., Effects of Physical Parameters on High Temperature Ultrasound Hyperthermia, Ultrasound in Med. & Biol. vol. 16, No. 4, pp. 409-420, 1990.

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhrol Dial Transplant, vol. 19, No. 6, 1354-1357 (2004).

Blum et al., Treatment of Ostial Renal-Artery Stenoses with Vascular Endoprostheses after Unsuccessful Balloon Angioplasty, N. Engl. J. Med. 336 459-65 (1997).

Bonsignore, C., "A Decade of Evolution in Stent Design", Proceedings of the International Conference on Shape Memory and Superelastic Technologies, (2003).

Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).

Bush et al., "Endovascular revascularization of renal artery stenosis: Technical and clinical results", Journal of Vascular Surgery, 2001, May, 1041-1049 (2001).

Camasao, D. B. et al., The mechanical characterization of blood vessels and their substitutes in the continuous quest for physiological-relevant performances: A critical review, Materials Today Bio, vol. 10 (2021).

Carter, J., "Microneurography and Sympathetic Nerve Activity: A Decade-By-Decade Journey across 50 Years," Journal of Neurophysiology, vol. 121, No. 4. doi: 10.1 152/jn.00570.2018.

Carter, Stefan et al., Measurement of Renal Artery Pressures by Catheterization in Patients with and without Renal Artery Stenosis, Circulation, vol. XXXIII, 443-449 (1966).

Chapelon, J. Y., "Treatment of Localised Prostate Cancer with Transrectal High Intensity Focused Ultrasound," European Journal of Ultrasound 9, 31-38, 1999.

Charlesworth, Peter et al., Renal Artery Injury from a Fogarty Balloon Catheter, Journal of Vascular Surgery, vol. 1, No. 4, 573-576 (1984).

Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Chiesa et al., Endovascular Stenting for the Nutcracker Phenomenon, J. Endovasc. Ther., 8:652-655 (2001).

Coates, Paul et al., "Time, Temperature, Power, and Impedance Considerations for Radiofrequency Catheter Renal Denervation," Cardiovascular Revascularization Medicine 42, 171-177 (2022).

Corrected Patent Owner's Response to Office Action, dated May 10, 2013, from File History of Inter Partes Reexamination U.S. Appl. No. 95/002,110.

Dangas, G. et al., Intravascular Ultrasound-Guided Renal Artery Stenting, J Endovasc Ther, 2001;8:238-247 (2001).

Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).

(56)        References Cited

OTHER PUBLICATIONS

Deardorff, Dana et al., Ultrasound Applicators with Internal Cooling for Interstitial Thermal Therapy, SPIE vol. 3594, 36-46, Jan. 1999.

Decision of the Patent Trial and Appeal Board in U.S. Appl. No. 14/731,347.

Declaration of Chris Daft dated Jan. 11, 2022, in the Patent Trial and Appeal Board, United States Patent and Trademark Office, Petition No. PTAB-IPR2022-00431.

Second Declaration of Chris Daft. Dated Jan. 10, 2023, in the Patent Trial and Appeal Board, United States Patent and Trademark Office, Petition No. PTAB-IPR2022-00431.

Declaration of Dr. Daniel van der Weide, dated Oct. 26, 2022, in the Patent Trial and Appeal Board, United States Patent and Trademark Office, Petition No. PTAB-IPR2022-00431.

Declaration of Dr. Dieter Haemmerich, dated Aug. 29, 2012, in the Patent Trial and Appeal Board, United States Patent and Trademark Office, In re Patent 7,717,948.

Declaration of Dr. John M. Moriarty in German Nullity proceedings for EP2261905 dated Jul. 13, 2022.

Declaration of Dr. John Moriarty, dated Jan. 19, 2023, in the Patent Trial and Appeal Board, United States Patent and Trademark Office, Petition No. PTAB-IPR2022-00431.

Declaration of Jonathan Bradford in Support of Patent Owner's Response, dated Oct. 27, 2022.

Declaration of Jonathan Bradford dated May 10, 2022, in the Patent Trial and Appeal Board, United States Patent and Trademark Office, Petition No. PTAB-IPR2022-00431.

Declaration of Dr. Michael Bohm dated Sep. 29, 2022 on behalf of Medtronic Inc.

Declaration of Dr. Robert Tucker, dated Oct. 27, 2022, in the Patent Trial and Appeal Board, United States Patent and Trademark Office, Petition No. PTAB-IPR2022-00431.

Declaration of Farrell Mendelsohn dated Jan. 10, 2022, in the Patent Trial and Appeal Board, United States Patent and Trademark Office, Petition No. PTAB-IPR2022-00431.

Defendant's Reply to Court Order of Oct. 4, 2022 and Plaintiff's Surrejoinder of Sep. 29, 2022 in the Mannheim District Court, case No. 7 O 14/21, dated Oct. 31, 2022.

Defendant's Response dated May 11, 2022 in the Munich Federal Patent Court, Nullity Suit 6 Ni 32/22.

Dibona, Gerald F., "Neural Control of the Kidney, Past, Present and Future," 41 [Part II] Hypertension 621 24 (2003).

Dibona, Gerald, Sympathetic Nervous System and Kidney in Hypertension, Current Opinion in Nephrology and Hypertension, vol. 11, 197-200 (2002).

Dibona, Gerald F. et al., "Neural Control of Renal Function", 77 Physiological Reviews No. 1, 75 (1997).

Diederich et al., "Catheter-based Ultrasound Applicators for Selective Thermal Ablation: progress towards MRI-guided applications in prostate," International Journal of Hyperthermia, 20:7, 739-756.

Diederich et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.

Diederich et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.

Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_ doi:10.1109fTBME.2002.807323.

Draney, Mary et al., Three-Dimensional Analysis of Renal Artery Bending Motion During Respiration, International Society of Endovascular Specialists, vol. 12, 380-386 (2005).

Erikson, Kenneth et al., Ultrasound in Medicine: A Review, IEEE Transactions on Sonics and Ultrasonics, vol. 21, No. 3 (1974).

EP Board of Appeals Communication dated Dec. 17, 2019— Preliminary Remarks for EP appeal No. T2680/16-3.3.4.01.

European Search Report in Application No. 12180431.4 dated Jan. 17, 2013.

European Communication in Application No. 12180431.4 dated Oct. 23, 2013.

European Office Action in Application No. 12180431.4.

European Patent No. 12167931, Claims of the Main Request dated Sep. 30, 2016.

European Search Report (Supplementary) in Application No. 14775754.6 dated Feb. 17, 2016.

European Search Report in Application No. 218186547 dated Nov. 19, 2018.

European Search Report in Application No. 20202272.9 dated Mar. 1, 2021.

Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.

Fengler, Karl et al., A Three-Arm Randomized Trial of Different Renal Denervation Devices and Techniques in Patients with Resistant Hypertension (Radiosound-HTN), 139 Circulation 590 (2019).

File History to EP1802370B1 Part 1.

File History to EP1802370B1 Part 2.

File History to EP1802370B1 Part 3.

Foley, Jessica L. et al., "Image-Guided HIFU Neurolysis of Peripheral Nerves to Treat Spasticity and Pain," Ultrasound in Med & Biol., vol. 30, Np. 9 pp. 1199-1207, 2004.

Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).

Gervais, Debra A. et al., Radiofrequency ablation of renal cell carcinoma: Part 2, Lessons learned with ablation of 100 tumors, 185 AJR Am. J. Roentgenol. 72 (2005) .

Goldberg, S. Nahum et al., EUS-guided radiofrequency ablation in the pancreas: results in a porcine model, 50 Gastrointest. Endosc. 392 (1999).

Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).

Gorsich, W., et al., Heat-Induced Contraction of Blood Vessels, Lasers in Surgery and Medicine, 2:1-13 (1982).

Gray, Henry, Gray's Anatomy: The Anatomical Basis of Medicine and Surgery, Churchill Livingstone, New York, NY (1995).

Habict, Antje et al., Sympathetic Overactivity and Kidneys, The Middle European Journal of Medicine, vol. 115, 634-640 (2003).

Hansen et al., The Transplanted Human Kidney Does Not Achieve Functional Reinnervation, 87 Clinical Science 13 (1994).

Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.

He, D. S. et al., Application of Ultrasound Energy for Intracardiac Ablation of Arrhythmias, European Heart Journal, vol. 16, 961-966 (1995).

Heffner, H. et al., "Gain, Band Width, and Noise Characteristics of the Variable-Parameter Amplifier," Journal of Applied Physics, vol. 29, No. 9, Sep. 1 958, 11 pgs.

Holmes, David R. et al., Pulmonary vein stenosis complicating ablation for atrial fibrillation: clinical spectrum and interventional considerations, 2 JACC Cardiovasc. Interv. 267 (2009).

Hsu, Thomas H. S. et al., Radiofrequency ablation of the kidney: acute and chronic histology in porcine model, 56 Urology 872 (2000).

Huang, S. K. S. et al., Radiofrequency Catheter Ablation of Cardiac Arrhythmias, Basic Concepts and Clinical Applications, Futura Publishing Company, Inc., Armonk, New York (2000).

Huang et al., Renal Denervation Prevents and Reverses Hyperinsulinemia-Induced Hypertension in Rats, Hypertension 32 (1998) pp. 249-254.

(56) References Cited

OTHER PUBLICATIONS

Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.

Isles et al., Management of Renovascular Disease: A Review of Renal Artery Stenting in Ten Studies, QJM 92, 159-67 (1999).

Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pgs.

Janssen, B. J. A. et al., "Renal nerves in hypertension." Miner Electrolyte Metab., 15:74-82 (1989).

Janzen, Nicolette et al., Minimally Invasive Ablative Approaches in the Treatment of Renal Cell Carcinoma, Current Urology Reports, vol. 3 (2002).

Kaltenbach, Benjamin et al., Renal Artery Stenosis After Renal Sympathetic Denervation, Journal of the American College of Cardiology, vol. 60, No. 25 (2012).

Kapural, Leonardo et al., "Radiofrequency Ablation for Chronic Pain Control," Anesthetic Techniques in Pain Management, pp. 517-525, 2001.

Katholi, R. E., et al., Importance of Renal Sympathetic Tone in the Development of DOCA-Salt Hypertension in The Rat, Hypertension, 2:266-273 (1980).

Kim, Yun-Hyeon et al., Pulmonary vein diameter, cross-sectional area, and shape: CT analysis, Radiology Society of North America, vol. 235, No. 1, 49-50 (2005).

Kirsh, Danielle, Balloon Catheters: What are some key design considerations?, Massdevice (Dec. 6, 2016).

Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).

Koomans, Hein et al., Sympathetic Hyperactivity in Chronic Renal Failure: A wake-up call, Frontiers in Nephrology, vol. 15, 524-537 (2004).

Kuo et al., "Atrial Fibrillation: New Horizons", Chang Gung Med J vol. 26 No. Oct. 10, 2003.

Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S. et al., Ardian: Succeeding Where Drugs Fail-Treating Hypertension in the Cath Lab, In Vivo, 27:23 (2009).

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Martin, Louis G. et al., Long-term Results of Angioplasty in 110 Patients with Renal Artery Stenosis, Journal of Vascular and Interventional Radiology, vol. 3, No. 4, 619-626 (1992).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pgs.

Matsumoto, Edward D. et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic Scientific Background, Hypertension and the Symplicity Renal Denervation System.

Medtronic, Symplicity RDN Common System Q&A.

Medtronic Inc., The Symplicity RDN System, 2012.

Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).

Millard et al., Renal Embolization for Ablation of Function In Renal Failure And Hypertension, Postgraduate Med. J. 65, 729-734 (1989).

Mitchell et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Nair et al., "The Need for and the Challenges of Measuring Renal Sympathetic Nerve Activity," Heart Rhythm 2016; 13:1166-1171.

Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T. et al., "Effects of long-term renal sympathetic denervation on heart failure after myocardial infarction in rats." Heart Vessels, 16:51-56 (2002).

Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Olsson, R. et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Osborn, J., "Catheter-Based Renal Nerve Ablation as a Novel Hypertension Therapy, Lost, and Then Found," in Translation.

Page, Irvine H. et al., The Effect of Renal Denervation on the Level of Arterial Blood Pressure and Renal Function in Essential Hypertension, 14 J. Clinical Investigation 27 (1935) (received for publication in 1934).

Page, Irvine H. et al., The Effect of Renal Denervation on Patients Suffering from Nephritis, 14 J. Clinical Investigation 443 (1935) (received for publication in 1935).

Papademetriou, Vasilios et al., Renal Sympathetic Denervation for the Treatment of Difficult-to-Control or Resistant Hypertension, 2011 Int. J. Hypertension, Article 196518 (2011).

(56) References Cited

OTHER PUBLICATIONS

Papademetriou et al., "Renal Sympathetic Denervation: Hibernation or Resurrection?", Cardiology 2016; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Pappone C et al., "Circumferential radiofrequency ablation of pulmonary vein ostia: a new anatomic approach for curing atrial fibrillation", Circulation. 2000; 102(21): 2619-2628. (2000).

Patent Owner's Amended Objections to Evidence Under 37 C.F.R. §42.64.

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

Patent Owner's Preliminary Response, filed May 10, 2022 in the Patent Trial and Appeal Board, United States Patent and Trademark Office, Petition No. PTAB-IPR2022-00431.

Patent Owner's Request for Oral Hearing, filed Mar. 23, 2023 in the Patent Trial and Appeal Board, United States Patent and Trademark Office, Petition No. PTAB-IPR2022-00431.

Patent Owner's Response, filed Oct. 27, 2022 in the Patent Trial and Appeal Board, United States Patent and Trademark Office, Petition No. PTAB-IPR2022-00431.

Patent Owner's Sur-Reply, filed Mar. 9, 2023 in the Patent Trial and Appeal Board, United States Patent and Trademark Office, Petition No. PTAB-IPR2022-00431.

Patent Owner's Updated Mandatory Notice, filed May 10, 2022 in the Patent Trial and Appeal Board, United States Patent and Trademark Office, Petition No. PTAB-IPR2022-00431.

Peet, M. M., Hypertension and Its Surgical Treatment by Bilateral Supradiaphragmatic Splanchnicectomy, Am. J. Surgery, LXXV:48-68 (1948).

Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.

Petitioner ReCor's Biography of Dr. Neil C. Barman.

Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.

Petitioner's Power of Attorney for Recor Medical, Inc., filed Jan. 13, 2022 in the Patent Trial and Appeal Board, United States Patent and Trademark Office, Petition No. PTAB-IPR2022-00431.

Petitioner Reply, filed Jan. 23, 2023 in the Patent Trial and Appeal Board, United States Patent and Trademark Office, Petition No. PTAB-IPR2022-00431.

Petitioners' Request for Oral Argument, filed Mar. 21, 2023 in the Patent Trial and Appeal Board, United States Patent and Trademark Office, Petition No. PTAB-IPR2022-00431.

Petitioners' Updated Mandatory Notices, dated Jan. 18, 2022 in the Patent Trial and Appeal Board, United States Patent and Trademark Office, Petition No. PTAB-IPR2022-00431.

Plaintiff's Nullity Brief, dated Jan. 14, 2022, in the Munich Federal Patent Court, Nullity Suit 6 Ni 32/22.

Plaintiff's Reply to the May 11, 2022 Response, dated Jul. 18, 2022, in the Munich Federal Patent Court, Nullity Suit 6 Ni 32/22.

Plaintiff's Response to Court Order disagreeing with Stay of Proceedings dated Oct. 28, 2022 in Mannheim District Court, Infringement suit 7 O 147/21.

Plaintiff's Technical Brief dated Sep. 29, 2022 in the Mannheim District Court, Infringement suit 7 O 147/21.

Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).

Prakash, Punit et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.

Prochnau, Dirk et al., Catheter-based renal denervation for drug-resistant hypertension by using a standard electrophysiology catheter, EuroIntervention, vol. 7, 1077-1080 (2012).

Pugsley et al., The vascular system: An overview of structure and function, Journal of Pharmacological and Toxicological Methods 44 (2000) 333-340.

Purerfellner, Helmut et al., Incidence, Management and Outcome in Significant Pulmonary Vein Stenosis Complicating Ablation for Atrial Fibrillation, 93 Am. J. Cardiol. 1428 (2004).

Pürerfellner, Helmut et al., Pulmonary vein stenosis following catheter ablation of atrial fibrillation, 20 Curr. Opin. Cardiol. 484 (2005).

Reaz, M. B. I. et al., "Techniques of EMG signal analysis: detection, processing, classification and applications," Biological Procedures Online, Jan. 2006, 25 pgs.

Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.

Romanes, G. J., Cunningham's Textbook of Anatomy (11th ed. 1972).

Ryan, Steve, What are the Risks Associated with a Pulmonary Vein Ablation Procedure?, Atrial Fibrillation: Resources for Patients (last accessed Oct. 18, 2022).

Ryan, Thomas et al., Proceedings of Thermal Treatment of Tissue with Image Guidance, Progress in Biomedical Optics, vol. 3594 (1999).

Ryan, Thomas P., Thermal Treatment of Tissue with Image Guidance; Ultrasound Catheters For Circumferential Cardiac Ablation 1999.

Sakakura, Kenichi et al., Anatomic Assessment of Sympathetic Peri-Arterial Renal Nerves in Man, Journal of the American College of Cardiology, vol. 64, No. 7, 635-643 (2014).

Salmanpour, A.et al., "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP.2010.5495604.

Sanchez-Quintana, Damian et al., How close are the phrenic nerves to cardiac structures? Implications for cardiac interventionalists, 16 J. Cardiovasc. Electrophysiol 309 (2005) ("Sánchez-Quintana").

Sato, Yu et al., "Translational Value of Preclinical Models for Renal Denervation: a histological comparison of human versus porcine renal nerve anatomy," EuroIntervention, 18, e1120-e1128, 2023.

Schmieder, Ronald E., Renal denervation in patients with chronic kidney disease: current evidence and future perspectives, Nephrol. Dial. Transplant. gfac189 (2022).

Schneider, Peter, Endovascular Skills: Guidewire and Catheter Skills for Endovascular Surgery, 2nd ed., Marcel Dekker, Inc., New York, NY (2003).

(56)            References Cited

OTHER PUBLICATIONS

Schneider, Peter A., Endovascular Skills, Quality Medical Publishing, Inc., 1998 ("Schneider").

Schmidt, Boris et al., "Pulmonary Vein Isolation by High Intensity Focused Ultrasound," Indian Pacing and Electrophysiology Journal, pp. 126-133 (2006).

Selected documents from the File History of Inter Partes Reexamination 95/002110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Shimizu, Kazumasa et al., Sympathetic Dysfunction in Heart Failure, Bailliere's Clinical Endocrinology and Metabolism, vol. 7, No. 2 (1993).

Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").

Slide deck from Medtronic Circulatory System Devices Panel Meeting, General Issues Panel: Clinical Evaluation of Anti-Hyperintensive Devices (Dec. 5, 2018).

Smithwick, R. H et al., "Splanchnicectomy for essential hypertension." J. Am. Med. Assoc., 152:1501-1504 (1953).

Stella, A. et al., "Effects of reversible renal denervation on haemodynamic and excretory functions of the ipsilateral and contralateral kidney in the cat." J Hypertension, 4: 181-188 (1986)("Stella").

Stipulation Modifying Schedule, dated Dec. 30, 2022 in the Patent Trial and Appeal Board, United States Patent and Trademark Office, Petition No. PTAB-IPR2022-00431.

Stipulation Modifying Schedule, dated Feb. 16, 2023 in the Patent Trial and Appeal Board, United States Patent and Trademark Office, Petition No. PTAB-IPR2022-00431.

Stoeckel, D. et al., A Survey of Stent Designs, Min Invas Ther & Allied Technol 2002: 11(4) 137-147 (2002).

Swartz, John F. et al., Radiofrequency Endocardial Catheter Ablation of Accessory Atrioventricular Pathway Atrial Insertion Sites, 87 Circulation 487 (1993).

Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07.012.

Tanaka, Kazushi et al., "A New Radiofrequency Thermal Balloon Catheter for Pulmonary Vein Isolation," Journal of the American College of Cardiology vol. 38, No. 7, 2001.

Teigen et al., Segmental Renal Artery Embolization for Treatment of Pediatric Renovascular Hypertension, J. Vasco Interv. Radiol. 3, 111-7 (1992).

Thatipelli, Mallik R. et al., CT angiography of renal artery anatomy for evaluating embolic protection devices, 18 J. Vasc. Interv. Radiol. 842 (2007).

The Doctors and Experts at WebMD, Webster's New World Medical Dictionary (3rd ed. 2008) ("WebsterMD").

Transcript of the Mar. 2, 2023 deposition of Dr. John Moriarty.

Transcript of the Mar. 3, 2023 deposition of Dr. Chris Daft.

Transcript of deposition of the Jan. 1, 2023 deposition of Dr. Robert Tucker.

Transcript of the Jan. 14, 2023 deposition of Dr. Daniel van der Weide.

Transcript of the Sep. 30, 2022 deposition of Dr. Chris Daft.

Transcript of the Oct. 1, 2022 deposition of Dr. Farrell Mendelsohn.

Tsao, Hsuan-Ming et al., Evaluation of Pulmonary Vein Stenosis after Catheter Ablation of Atrial Fibrillation, 6 Card. Electrophysiol. Rev. 397 (2002).

Turner et al., "Initial Experience Using the Palmaz Corinthian Stent for Right Ventricular Outflow Obstruction in Infants and Small Children", Catheterization and Cardiovascular Interventions 51:444-449 (2000).

Uchida et al., "Effect of radiofrequency catheter ablation on parasympathetic denervation: A comparison of three different ablation sites." PACE, 21 :2517- 2521 (1998).

Ulmsten, Ulf et al., "The Safety and Efficacy of Meno TreatTM, a new balloon device for thermal endometrial ablation," Acta Obstet Gynecol Scand 2001; 80: 52-57.

Vaezy, Shahram et al., Image-Guided Acoustic Therapy, Annual Review Biomedical Engineering, vol. 3, 375-390 (2001).

Valente, John F et al., Laparoscopic renal denervation for intractable ADPKD-related pain, 16 Nephrol. Dial. Transplant. 160 (2001).

Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").

Wanchoo, Nishey, Medtronic Gets European and Australian Approval for Symplicity Spyral Multi-Electrode Renal Denervation Catheter, Medgadget (2013).

Weinstock, Marta et al., "Renal Denervation Prevents Sodium Retention and Hypertension in Salt-Sensitive Rabbits with Genetic Baroreflex Impairment", 90 Clinical Science 287 (1996).

Xu, J. et al., "A Bidirectional Neuromodulation Technology for Nerve Recording and Stimulation, Micromachines," vol. 9, 1 1 538. Oct. 23, 2018. doi:10.3390/mi9110538.

Xu, J. et al., "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

Zazgornik, "Bilateral Nephrectomy: The best, but often overlooked, treatment for refractory hypertension in hemodialysis patients," Am. J. Hypertension, 11:1364-1370 (1998).

Ziegler et al., Sources of Urinary Catecholamines in Renal Denervated Transplant Recipients, 8 J. Hypertension No. 10, 927 (1990).

U.S. Appl. No. 10/408,665, File History.

U.S. Appl. No. 11/532,814, Non-Final Office Action mailed Mar. 29, 2012, 15 pgs.

U.S. Appl. No. 14/683,966, Non-Final Office Action mailed Jun. 12, 2017, 14 pgs.

U.S. Appl. No. 14/683,966, Response filed Nov. 10, 2017 to Non-Final Office Action mailed Jun. 12, 2017, 13 pgs.

U.S. Appl. No. 14/683,966, Notice of Allowance mailed Jan. 31, 2018, 8 pgs.

U.S. Appl. No. 14/683,966, PTO Response to Rule 312 Communication mailed Mar. 29, 2018, 2 pgs.

U.S. Appl. No. 14/683,966, 312 Amendment filed Mar. 13, 2018, 10 pgs.

U.S. Appl. No. 14/683,966, Corrected Notice of Allowance mailed May 22, 2018, 4 pgs.

U.S. Appl. No. 15/204,349, Preliminary Amendment filed Nov. 30, 2016, 3 pgs.

U.S. Appl. No. 15/204,349, Restriction Requirement mailed May 17, 2018, 7 pgs.

U.S. Appl. No. 15/204,349, Response filed Jun. 5, 2018 to Restriction Requirement mailed May 17, 2018, 7 pgs.

U.S. Appl. No. 15/204,349, Non-Final Office Action mailed Nov. 27, 2018, 14 pgs.

U.S. Appl. No. 15/204,349, Response filed Feb. 27, 2019 to Non-Final Office Action mailed Nov. 27, 2018, 10 pgs.

U.S. Appl. No. 15/204,349, Final Office Action mailed Apr. 22, 2019, 16 pgs.

U.S. Appl. No. 15/204,349, Response filed Jun. 24, 2019 to Final Office Action mailed Apr. 22, 2019, 12 pgs.

U.S. Appl. No. 15/204,349, Advisory Action mailed Jul. 9, 2019, 5 pgs.

U.S. Appl. No. 15/261,732, Notice of Allowance dated Sep. 25, 2018, 7 pgs.

U.S. Appl. No. 15/299,694, Restriction Requirement mailed Aug. 6, 2018, 6 pgs.

U.S. Appl. No. 15/299,694, Response filed Oct. 8, 2018 to Restriction Requirement mailed Aug. 6, 2018, 7 pgs.

U.S. Appl. No. 15/299,694, Non-Final Office Action mailed Nov. 27, 2018, 15 pgs.

U.S. Appl. No. 15/299,694, Response filed Feb. 27, 2019 to Non-Final Office Action mailed Nov. 27, 2018, 10 pgs.

U.S. Appl. No. 15/299,694, Final Office Action mailed Apr. 22, 2019, 16 pgs.

(56) References Cited

OTHER PUBLICATIONS

U.S. Appl. No. 15/299,694, Response filed Jun. 24, 2019 to Final Office Action mailed Apr. 22, 2019, 11 pgs.

U.S. Appl. No. 15/299,694, Advisory Action mailed Jul. 9, 2019, 5 pgs.

U.S. Appl. No. 15/943,354, Preliminary Amendment filed Apr. 3, 2018, 9 pgs.

U.S. Appl. No. 15/943,354, Restriction Requirement mailed Nov. 20, 2019, 8 pgs.

U.S. Appl. No. 15/943,354, Response filed Dec. 19, 2019 to Restriction Requirement mailed Nov. 20, 2019, 8 pgs.

U.S. Appl. No. 15/943,354, Non-Final Office Action mailed Jan. 13, 2020, 6 pgs.

U.S. Appl. No. 15/943,354, Non-Final Office Action mailed Apr. 20, 2020, 7 pgs.

U.S. Appl. No. 15/996,978, Preliminary Amendment filed Jun. 5, 2018, 11 pgs.

U.S. Appl. No. 15/996,978, Restriction Requirement mailed Feb. 7, 2020, 7 pgs.

U.S. Appl. No. 15/996,978, Response filed Apr. 6, 2020 to Restriction Requirement mailed Feb. 7, 2020, 8 pgs.

U.S. Appl. No. 15/996,978, Restriction Requirement mailed Apr. 16, 2020, 8 pgs.

U.S. Appl. No. 15/996,978, Response filed May 1, 2020 to Restriction Requirement mailed Apr. 16, 2020, 8 pgs.

U.S. Appl. No. 15/996,978, Non-Final Office Action mailed Jun. 11, 2020, 8 pgs.

U.S. Appl. No. 15/996,978, Final Office Action mailed Feb. 19, 2021, 6 pgs.

U.S. Appl. No. 15/996,978, Response to Office Action filed May 18, 2021, 14 pgs.

U.S. Appl. No. 15/996,978, Final Office Action mailed Jun. 16, 2021, 12 pgs.

U.S. Appl. No. 15/996,978, Response to Office Action filed Jul. 20, 2021, 15 pgs.

U.S. Appl. No. 15/996,978, Non-Final Office Action mailed Sep. 2, 2021, 13 pgs.

U.S. Appl. No. 15/996,978, Response to Office Action filed Sep. 22, 2021, 19 pgs.

U.S. Appl. No. 15/996,978, Notice of Allowance mailed Oct. 6, 2021, 7 pgs.

U.S. Appl. No. 16/219,874, Final Office Action mailed Dec. 21, 20, 7 pgs.

U.S. Appl. No. 16/517,180, Preliminary Amendment filed Jul. 19, 2019, 12 pgs.

Ahmed, Muneeb et al., "Thermal Ablation Therapy for Hepatocellular Carcinoma," J. Vasc. Interv, Radiol., vol. 13, No. 9 pt. 2, 2002.

Benito, Fernando et al., "Radiofrequency catheter ablation of accessory pathways in infants," Heart, vol. 78, p. 160-162, 1997.

Chang, Isaac A. et al., "Thermal Modeling of Lesion Growth with Radiofrequency Ablation Devices," Biomedical Engineering Online vol. 3, p. 27, 2004.

Chung, Andrew et al., "Thermal dosimetry of a focused ultrasound beam in vivo by magnetic resonance imaging," Medical Physics, vol. 26, No. 9, p. 2017-2026, Sep. 1999.

Damianou, Christakis et al., "High Intensity Focused Ultrasound Ablation of Kidney Guided MRI," Ultrasound in Med. & Biol., vol. 30, No. 3, p. 397-404, 2004.

Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.

Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.

Diederich, Chris J. et al., "Ultrasound Technology for Hyperthermia," Ultrasound in Med. & Biol., vol. 25, No. 6, p. 871-887, 1999.

Fry, F.J. et al., "Production of Reversible Changes in the Central Nervous System by Ultrasound," Science, vol. 127, p. 83-84, Jan. 1958.

Gavrilov, L.R. et al., The Effect of Focused Ultrasound on the Skin and Deep Nerve Structures of Man and Animal, p. 279-292.

Gavrilov, L.R., "Use of Focused Ultrasound for Stimulation of Nerve Structures," Ultrasonics, p. 132-138, May 1984.

Graham, S.J. et al., "Quantifying Tissue Damage Due to Focused Ultrasound Heating Observed by MRI" Magnetic Resonance in Medicine vol. 41, p. 321-328, 1999.

Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.

Häacker, Axel et al., "Extracorporeal Organotripsy for Renal Tumours," Current Opinion in Urology, vol. 13, p. 221-225, 2003.

Hausberg, Martin et al., "Sympathetic Nerve Activity in End-Stage Renal Disease," Circulation, vol. 106, p. 1974-1979, 2002.

Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.

Israel, Gary M. et al., "MRI of the Kidney and Urinary Tract," Journal of Magnetic Resonance Imaging, vol. 24, p. 725-734, 2006.

Jiang, S.C. et al., "Effects of Thermal Properties and Geometrical Dimensions on Skin Burn Injuries," Burns, vol. 28, p. 713-717, 2002.

Kaye, David M. et al., "Functional and Neurochemical Evidence for Partial Cardiac Sympathetic Reinnervation After Cardiac Transplantation in Humans," Circulation, vol. 88, No. 3, Sep. 1993.

Keane, David, "New Catheter Ablation Techniques for the Treatment of Cardiac Arrhythmias," Cardiac Electrophysiology Review vol. 6, No. 4, p. 341-348, 2002.

Kennedy, J.E. et al., "High Intensity Focused Ultrasound: Surgery of the Future?", The British Journal of Radiology, vol. 76, p. 590-599, Sep. 2003.

Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.

Lauder, Lucas et al., "Renal Denervation in the Management of Hypertension," EuroIntervention, vol. 20, pg. e467-e478, 2024.

Lele, P.P., "Effects of Focused Ultrasonic Radiation on Peripheral Nerve, with Observations on Local Heating," Experimental Neurology, vol. 8, p. 47-83, 1963.

Liao, Qingyao et al., "Optimal Strategy for HIFU-Based Renal Sympathetic Denervation in Canines," Frontiers in Cardiovascular Medicine vol. 8, p. 1-11, Oct. 2021.

Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.

Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.

Mahfoud, Felix et al., "Device Therapy of Hypertension," Circulation Research nol. 128, p. 1080-1099, Apr. 2021.

Makin, Inder Raj. S. et al., "Miniaturized Ultrasound Arrays for Interstitial Ablation and Imaging," Ultrasound in Med. & Biol. vol. 31, No. 11, p. 1539-1550, 2005.

Malcolm, A.L. et al., "Ablation of Tissue Volumes Using High Intensity Focused Ultrasound" Ultrasound in Med. & Biol. vol. 22 No. 5 p. 659-669, 1996.

Manolis, Antonis S et al., "Radiofrequency Catheter Ablation for Cardiac Tachyarrhythmias," Annals of Internal Medicine, vol. 131, No. 6, p. 452-461, Sep. 1994.

Mitchell, G.A.G et al., "An Anatomical Evaluation of Operations for Hypertension," Proceedings of the Anatomical Society vol. LIV., No. 10, p. 545-560.

Mompeo, Blanca et al., "The Gross Anatomy of the Renal Sympathetic Nerves Revisited," Clinical Anatomy vol. 29, p. 660-664, Apr. 2016.

(56)                    References Cited

OTHER PUBLICATIONS

Moore, J.H. et al., "The Biophysical Effects of Ultrasound on Median Nerve Distal Latencies," Electromyogr. Clin. Neurophysiol., vol. 40, p. 169-190, 2000.

Nath, Sunil et al., "Basic Aspects of Radiofrequency Catheter Ablation," Journal of Cardiovascular Electrophysiology vol. 5, No. 10, p. 863-876, Oct. 1994.

Nath, Sunil et al., "Biophysics and Pathology of Catheter Energy Delivery Systems," Progress in Cardiovascular Diseases, vol. XXXVII, No. 4, p. 185-204, Jan./Feb. 1995.

Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.

Nikfarjam, Mehrdad et al., "Mechanisms of Focal Heat Destruction of Liver Tumors," Journal of Surgical Research, vol. 127, No. 2, p. 208-223, Aug. 2005.

Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.

Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.

Papademetriou, Vasilios et al., "Renal Nerve Ablation for Resistant Hypertension, How Did We Get Here, Present Status, and Future Directions," Circulation, No. 129, p. 1440-1451, 2014.

Pozzoli, Alberto et al., "Electrophysiological Efficacy of Epicor High-Intensity Focused Ultrasound," European Journal of Cardio-Thoracic surgery, vol. 42, p. 129-134, 2012.

Riis, Thomas et al., "Effective Ultrasonic Stimulation in Human Peripheral Nervous System," IEE Transactions on Biomedical Engineering, vol. XX, No. XX, p. 1-8, XXXX 2021.

Roux, N. et al., "The Myocardial Sleeves of the Pulmonary Veins: Potential Implications for Atrial Fibrillation," Surg. Radiol. Anat., vol. 26, p. 285-289, Feb. 2004.

Schuarte, Patrick et al., "Catheter Ablation of Cardiac Autonomic Nerves for Prevention of Vagal Atrial Fibrillation," Circulation vol. 102, p. 2774-2780, 2000.

Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.

Ter Haar, G., "Ultrasound Focal Beam Surgery," Ultrasound in Med. & Biol., vol. 21, No. 9, p. 1089-1100, 1995.

Ter Haar, G.R. et al., "Ultrasonic Heating of Mammalian Tissues In vivo," Br. J. Cancer vol. 45, Supp. V., p. 65-67, 1982.

Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.

Trippodo, Nick C. et al., "Similarities of Genetic (Spontaneous) Hypertension," Circulation Research vol. 48, No. 3, p. 309-319, Mar. 1981.

Urban, Bruce A. et al., "Three-dimensional Volume-rendered CT Angiography of the Renal Arteries and Veins: Normal Anatomy, Variants, and Clinical Applications," RG vol. 21 no. 2, p. 373-386, Mar.-Apr. 2001.

Wang, Shyh-Hau et al., "Effects of Low Intensity Ultrasound on the Conduction Property of Neural Tissues," IEEE International Ultrasonics, Ferroelectrics, and Frequency Control Joint 50th Anniversary Conference, p. 1824-1827, 2004.

Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.

Wells, P.N.T., "Functional Modification: Clinical Applications," Biomedical Ultrasonics, p. 470-504, 1977.

Winternitz, Sherry R. et al., "Importance of the Renal Nerves in the Pathogenesis of Experimental Hypertension," Hypertension (supp. III), vol. 4, No. 5, p. III-08-III-115, Sep.r-Oct. 1982.

Wulff, V.J. et al., "Effects of Ultrasonic Vibrations on Nerve Tissues," P.S.E.B.M., vol. 76, p. 361-366, 1951.

Yarmolenko, Pavel S. et al., "Thresholds for thermal damage to normal tissues: An update," Int. J. Hyperthermia, vol. 27 No. 4, p. 320-343, Jun. 2011.

Young, Robert R. et al., "Functional Effects of Focused Ultrasound on Mammalian Nerves," Science, vol. 134, p. 1521-1522, Nov. 1961.

Zimmer, J.E. et al., "The Feasibility of Using Ultrasound for Cardiac Ablation," IEEE Transactions on Biomedical Engineering, vol. 42, No. 9, p. 891-897, Sep. 1995.

Office Action for Taiwanese Patent Application No. 112144098, mailed Jun. 16, 2025, 14 pages.

Correspondence from PTAB Deputy Chief Clerk to Counsel re conference call request-Exhibit 3001 in the Patent Trial and Appeal Board, United States Patent and Trademark Office, Petition No. PTAB-IPR2022-00431, May 26, 2022, 2 pages.

Curriculum Vitae of Dr. John M. Moriarty, Jun. 2022, 28 pages.

Curriculum Vitae of Farrell Mendelsohn, 6 pages.

U.S. Appl. No. 60/415,575, filed Oct. 3, 2002, File History.

U.S. Appl. No. 60/442,970, filed Jan. 29, 2003, File History.

U.S. Appl. No. 60/616,254, filed Oct. 5, 2004, File History.

U.S. Appl. No. 60/624,793, filed Nov. 2, 2004, File History.

U.S. Appl. No. 60/747,137, filed May 12, 2006, File History.

U.S. Appl. No. 60/808,306, filed May 25, 2006, File History.

U.S. Appl. No. 60/816,999, filed Jun. 28, 2006, File History.

U.S. Appl. No. 61/405,472, filed Oct. 21, 2010, File History.

U.S. Appl. No. 12/754,337, filed Apr. 5, 2010, File History.

U.S. Pat. No. 10,039,901 issued Aug. 7, 2018, File History.

U.S. Pat. No. 9,943,666 issued Apr. 17, 2018, File History.

U.S. Pat. No. 9,981, 108 issued May 29, 2018, File History.

U.S. Appl. No. 17/453,636, filed Nov. 4, 2021, File History.

Schlaich, M.P. et al., "Renal Denervation: A Potential New Treatment Modality for Polycystic Ovary Syndrome," Journal of Hypertension, vol. 29, No. 5, pp. 991-996, May 2011, doi:10.1097/HJH. 0b013e328344db3a.

INSERT A SHAPING MANDREL INTO AN ISOLATION TUBE LUMEN OF AN ISOLATION TUBE    2502

HEAT SET THE ISOLATION TUBE SUCH THAT A JOG OF THE SHAPING MANDREL IS SET IN THE ISOLATION TUBE    2504

INSERT THE ISOLATION TUBE INTO A GUIDEWIRE LUMEN OF A CATHETER SHAFT    2506

TISSUE TREATMENT CATHETER HAVING SUPPORTIVE ISOLATION TUBE

This application claims the benefit of priority of U.S. Provisional Patent Application No. 63/383,816, filed on Nov. 15, 2022, titled "TISSUE TREATMENT CATHETER HAVING SUPPORTIVE ISOLATION TUBE," which is incorporated herein by reference in its entirety to provide continuity of disclosure.

BACKGROUND

Field

This application relates generally to minimally-invasive apparatuses, systems, and methods that provide energy delivery to a targeted anatomical location of a subject, and more specifically, to catheter-based, intraluminal apparatuses for the treatment of tissue, such as nerve tissue.

Background Information

According to the Centers for Disease Control and Prevention (CDC), about one in every three adults suffer from high blood pressure, also known as hypertension. Left untreated, hypertension can result in renal disease, arrhythmias, and heart failure. In recent years, the treatment of hypertension has focused on minimally invasive interventional approaches to inactivate the renal nerves surrounding the renal artery. Autonomic nerves tend to follow blood vessels to the organs that they innervate. Catheters may reach specific structure that may be proximate to the lumens in which they travel. For example, one system employs a radio frequency (RF) generator connected to a catheter having multiple electrodes placed against the intima of the renal artery, which are used to create an electrical field in the vessel wall and surrounding tissue that results in resistive (ohmic) heating of the tissue to a temperature sufficient to ablate the tissue and the renal nerve passing through that tissue. To treat all the renal nerves surrounding the renal arteries, the RF electrodes are repositioned several times around the inside of the renal artery. However, the relatively confined electric fields created by the RF electrodes may miss some of the renal nerves, leading to an incomplete treatment. Additionally, to heat the renal nerves, the RF electrodes must contact the intima, posing a risk of damage or necrosis to the intima, which in turn can lead to thrombus formation, fibrosis of the vessel wall, mechanical weakening of the vessel and possible vessel dissection.

Another approach to renal nerve deactivation is the use of high-intensity focused ultrasound (HIFU), which relies on vibrational energy to cause frictional heating and disruption of the tissue, and in turn, raise the tissue temperature sufficiently to cause ablation or remodeling.

U.S. Pat. Nos. 9,943,666, 9,981,108, and 10,039,901 to Warnking, U.S. Pat. Nos. 9,700,372, 9,707,034, and 10,368, 944 to Schaer, and U.S. Pat. Nos. 10,350,440 and 10,456, 605 to Taylor, the entire contents of each of which is incorporated by reference herein, disclose a system that uses unfocused ultrasound to ablate nerves. Embodiments of the system include an ultrasound transducer positioned along a distal end of a catheter designed to be inserted into a blood vessel (e.g., the renal artery). Electrical cabling, which is received within a cabling lumen of the catheter, can be used to power the ultrasound transducer. The ultrasound transducer emits one or more therapeutic doses of unfocused ultrasound energy, which heats the tissue adjacent to the body lumen within which the transducer is disposed. The system may also include a balloon mounted at the distal end of the catheter used to circulate cooling fluid both prior to, during, and after activation of the transducer to cool the transducer and help prevent thermal damage to the interior surface of the blood vessel wall while the nerves are being heated and damaged at depth. Circulation of the cooling fluid occurs through two fluid lumens—an input fluid lumen that carries fluid distally to the balloon, and an output fluid lumen that returns fluid proximally from the balloon.

Such a design enables creation of one or more ablation zones sufficient to achieve long-term nerve inactivation at different locations around the circumference of the blood vessel, thereby treating a patient's hypertension while mitigating damage to the blood vessel and surrounding organs.

The ultrasound transducer may include first and second electrodes which are arranged on either side of a cylindrical piezoelectric material, such as lead zirconate titanate (PZT). To energize the transducer, a voltage is applied across the first and the second electrodes at frequencies selected to cause the piezoelectric material to resonate, thereby generating vibration energy that is emitted radially outward from the transducer. The transducer is designed to provide a generally uniform and predictable emission profile.

SUMMARY

The present invention is defined in the independent claims. Further embodiments of the invention are defined in the dependent claims.

A tissue treatment catheter is provided herein. The tissue treatment catheter includes a catheter shaft, a balloon, an ultrasound transducer, and an isolation tube. The catheter shaft has a distal shaft end, a fluid lumen, a guidewire port, and a guidewire lumen. The guidewire lumen extends from the distal shaft end to the guidewire port. The balloon is mounted on the catheter shaft and has an interior in fluid communication with the fluid lumen. The ultrasound transducer is located in the interior and has a transducer lumen. The isolation tube extends through the transducer lumen and the guidewire lumen to a proximal tube end between the distal shaft end and the guidewire port.

A tissue treatment catheter is provided herein. The tissue treatment catheter includes a catheter shaft, a balloon, an ultrasound transducer, and an isolation tube. The catheter shaft has a central axis, a fluid lumen, and a guidewire lumen. The guidewire lumen has a lumen axis radially offset from the central axis. The balloon is mounted on the catheter shaft and has an interior in fluid communication with the fluid lumen. The ultrasound transducer is disposed in the interior and has a transducer lumen. The central axis extends through the transducer lumen. The isolation tube extends through the transducer lumen along the central axis and through the guidewire lumen along the lumen axis.

A tissue treatment catheter is provided herein. The tissue treatment catheter includes a catheter shaft, a balloon, an ultrasound transducer, a lumen hub, and an electrical connector. The catheter shaft has a first fluid lumen, a second fluid lumen, and a cable lumen. The balloon is mounted on the catheter shaft and has an interior in fluid communication with the first fluid lumen and the second fluid lumen. The ultrasound transducer is in the interior. The lumen hub is coupled to the catheter shaft and includes a first fluid tube in fluid communication with the first fluid lumen and a second fluid tube in fluid communication with the second fluid lumen. The first fluid tube and the second fluid tube extend outward from a longitudinal axis of the catheter shaft in a wye configuration. The electrical connector is coupled to the lumen hub radially between the first fluid tube and the second fluid tube.

A method is provided herein. The method includes inserting an isolation tube of a distal catheter subassembly into a guidewire lumen of a catheter shaft of a medial catheter subassembly. The distal catheter subassembly includes an ultrasound transducer mounted on the isolation tube and a balloon containing the ultrasound transducer. The catheter shaft includes a first fluid lumen and a second fluid lumen in fluid communication with an interior of the balloon. The method includes bonding an electrical cable of the medial catheter subassembly to a mending board of a proximal catheter subassembly. The proximal catheter subassembly includes a connector housing containing the mending board, and an extension cable wire extending proximally from the mending board to a proximal connector.

A method is provided herein. The method includes inserting a shaping mandrel into an isolation tube lumen of an isolation tube. The shaping mandrel includes a mandrel jog. The isolation tube includes a core tube having a tie layer. The method includes heat setting the isolation tube such that the jog is set in one or more of the core tube or the tie layer. The method includes inserting the isolation tube into a guidewire lumen of a catheter shaft.

A tissue treatment catheter is provided herein. The tissue treatment catheter includes a catheter shaft having a distal shaft end, a guidewire port, and a guidewire lumen. The guidewire lumen extends from the distal shaft end to the guidewire port. The tissue treatment catheter includes a transducer having a transducer lumen. The tissue treatment catheter includes an isolation tube extending through the transducer lumen and the guidewire lumen to the guidewire port. The isolation tube includes a jog. The jog is longitudinally between the transducer and the catheter shaft.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

DETAILED DESCRIPTION

Figure 1:
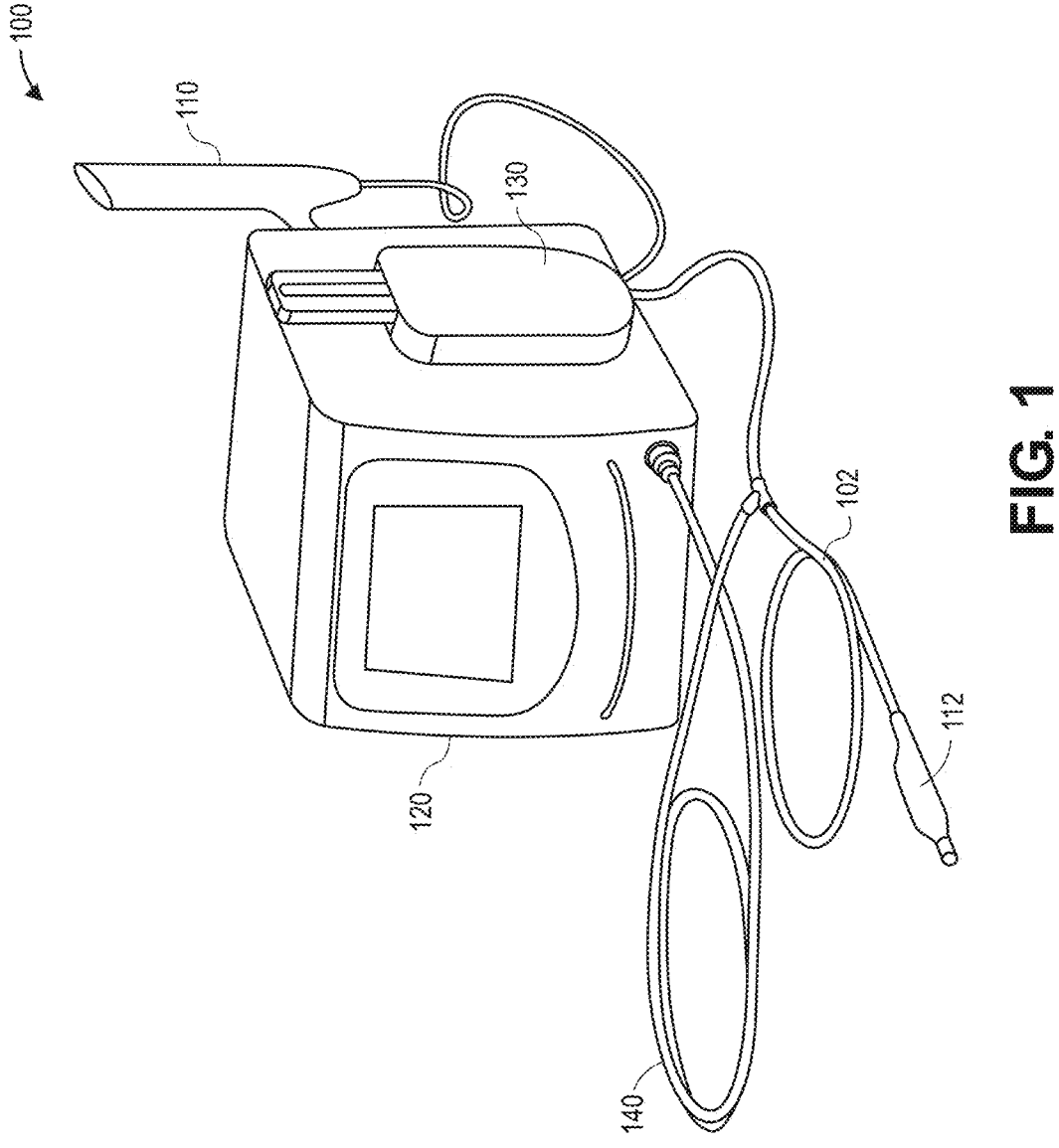
FIG. 1 is a perspective view of a tissue treatment system, in accordance with an embodiment.

Systems that use unfocused ultrasound energy to treat tissue, and methods of using the same are provided herein. In certain embodiments, acoustic-based tissue treatment transducers, apparatuses, systems, and portions thereof, are provided. The systems may be catheter-based. The systems may be delivered intraluminally (e.g., intravascularly) so as to place a transducer within a target anatomical region of the subject, for example, within a suitable body lumen such as a blood vessel. Once properly positioned within the target anatomical region, the transducer can be activated to deliver unfocused ultrasonic energy radially outward so as to suitably heat, and thus treat, tissue within the target anatomical region. The transducer or piezoelectric material can be activated at a frequency, duration, and energy level suitable for treating the targeted tissue. In one non-limiting example, unfocused ultrasonic energy generated by the transducer or piezoelectric material or radio frequency (RF) energy transmitted by the electrodes may target select nerve tissue of the subject, and may heat such tissue in such a manner as to neuromodulate (e.g., fully or partially ablate, necrose, or stimulate) the nerve tissue.

In a manner such as described in the Warnking, Schaer, and Taylor patents mentioned above, neuromodulating renal nerves may be used to treat various conditions, e.g., hypertension, chronic kidney disease, atrial fibrillation, autonomic nervous system for use in treating a variety of medical conditions, arrhythmia, heart failure, end stage renal disease, myocardial infarction, anxiety, contrast nephropathy, diabetes, metabolic disorder and insulin resistance, etc. It should be appreciated, however, that the balloon catheters suitably may be used to treat other nerves and conditions, e.g., sympathetic nerves of the hepatic plexus within a hepatic artery responsible for blood glucose levels important to treating diabetes, or any suitable tissue, e.g., heart tissue triggering an abnormal heart rhythm, and is not limited to use in treating (e.g., neuromodulating) renal nerve tissue. In another example, a tissue treatment catheter is used to ablate sympathetic nerves of the renal arteries and a hepatic artery to treat diabetes or other metabolic disorders. In certain embodiments, the tissue treatment catheters are used to treat an autoimmune and/or inflammatory condition, such as rheumatoid arthritis, sepsis, Crohn's disease, ulcerative colitis, and/or gastrointestinal motility disorders by neuromodulating sympathetic nerves within one or more of a splenic artery, celiac trunk, superior or inferior mesenteric artery. In certain embodiments, the tissue treatment catheter is used to ablate nerve fibers in the celiac ganglion and/or renal arteries to treat hypertension. In certain embodiments, the transducers are used to treat pain, such as pain associated with pancreatic cancer, by, e.g., neuromodulating nerves that innervate the pancreas. Ultrasound or RF energy may also be used to ablate nerves of both the pulmonary vein and the renal arteries to treat atrial fibrillation. In still other examples, ultrasound or RF energy may additionally or alternatively be used to ablate nerves innervating a carotid body in order to treat hypertension and/or chronic kidney disease.

In an aspect, an isolation tube of a tissue treatment catheter is lengthened. When tracking a catheter having an isolation tube through a vasculature, the isolation tube can be tracked over a guidewire. The guidewire can interact with, e.g., slide against, the isolation tube and a catheter shaft. This interaction can result in the catheter shaft binding the guidewire, causing "guidewire entrapment," and reducing trackability. Extending the isolation tube proximally from the transducer to a location near or at a guidewire port of the catheter, as described below, can influence guidewire tracking to avoid guidewire entrapment. More particularly, the lengthened isolation tube provides a guidewire lumen that guides the guidewire through the catheter and can reduce a likelihood of the catheter impinging or binding on the guidewire.

In an aspect, a jog is included in an isolation tube of a tissue treatment catheter. In certain catheter configurations, such as in a rapid exchange (RX) version of a tissue treatment catheter, a guidewire may be uncentered within the catheter body. The uncentered guidewire can deflect a transducer. For example, the guidewire can push the transducer, through which the guidewire extends, off center also. The deflected transducer can tilt outward, causing uneven energy delivery to the vessel wall. The jog, on the other hand, can center the isolation tube, and the guidewire that extends through the isolation tube, at a distal end of the catheter. The centered isolation tube can therefore support the transducer at a centered location and reduce a likelihood of transducer tilting. Accordingly, uniform energy delivery to the vessel wall may be achieved.

In an aspect, a proximal catheter subassembly of a tissue treatment catheter includes an extension cable that extends proximally from a lumen hub at the proximal end of the catheter. When a bulky cable is attached to a proximal end of a catheter, the bulky cable can pull on the catheter. The loading from the cable can complicate handling of the catheter and/or cause the catheter to fall from the operating table. By contrast, the extension cable of the proximal catheter subassembly described below can include a lightweight, low profile cable that acts as a transition between the catheter and an external cable. The external cable can be bulkier than the extension cable. The external cable, however, can be distanced from the catheter by the lightweight extension cable, and is therefore less likely to pull on the catheter. Handling of the catheter may therefore be improved, and it may be less likely that the catheter will be pulled off of the operating table.

In an aspect, a tissue treatment catheter has a modular construction. The modular construction can be implemented in which subassemblies are separately manufactured and then brought together to build the catheter. The catheter construction can facilitate such a modular construction. For example, a lumen hub of a medial catheter subassembly can include a cutout to receive an electrical connector of a proximal catheter subassembly. The modular construction may also be facilitated in part by the incorporation of a proximal catheter subassembly having a mending board. The mending board can have electrically interconnected contacts exposed for quick, efficient soldering to a twisted wire pair of the proximal catheter subassembly and/or a coaxial cable of the medial catheter subassembly. The modular construction can facilitate manufacturability and increase production throughput as compared to manufacturing a catheter from individual components, as is typically done.

Referring to FIG. 1, a tissue treatment system is illustrated in accordance with an embodiment. The tissue treatment system 100 is shown as including a tissue treatment catheter 102, a controller 120, and a connection cable 140. In certain embodiments, as described below, the tissue treatment catheter 102 includes an ultrasound transducer within a balloon 112. The tissue treatment system 100 can include a reservoir 110, a fluid transfer cartridge, and a control mechanism, such as a handheld remote control, operative to control circulation of a cooling fluid to inflate the balloon 112 within a target anatomy and to control activation of the ultrasound transducer to deliver energy to the target anatomy.

In the embodiment shown in FIG. 1, the controller 120 is shown as being connected to the catheter through the cartridge and the connection cable 140. In certain embodiments, the controller 120 interfaces with the cartridge to provide a cooling fluid to the catheter for selectively inflating and deflating the balloon 112. The balloon 112 can be made from, e.g., nylon, a polyimide film, a thermoplastic elastomer (such as those marked under the trademark PEBAX™), a medical-grade thermoplastic polyurethane elastomer (such as Pellethane®, Isothane®, or other suitable polymers or any combination thereof), but is not limited thereto.

Figure 2:
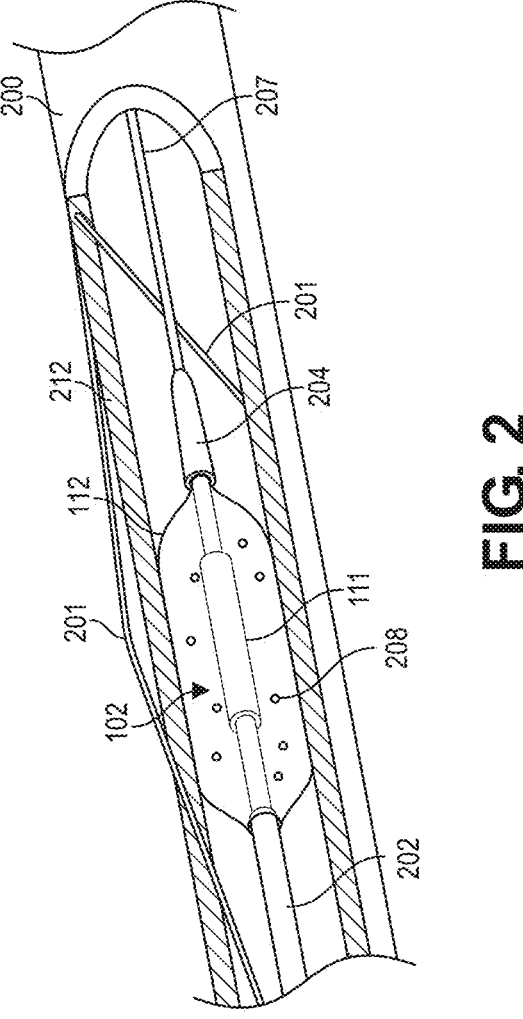
FIG. 2 is a perspective view of a tissue treatment catheter inserted into a body lumen, in accordance with an embodiment.

Referring to FIG. 2, a perspective view of a tissue treatment catheter inserted into a body lumen, is illustrated in accordance with an embodiment. A distal portion of the tissue treatment catheter 102 may be inserted into the body lumen of a subject. The body lumen may be a blood vessel, e.g., a renal artery, that has several nerves 201 in an outer layer, e.g., adventitia layer, of the blood vessel. The distal portion of the tissue treatment catheter 102 may include an ultrasound transducer 111, the balloon 112 filled with a cooling fluid 208, a catheter shaft 202, and/or a guidewire support tip 204 configured to receive a guidewire 207.

The transducer 111 may be disposed partially or completely within the balloon 112, which may be inflated with the cooling fluid 208, e.g., water, dextrose, or saline, so as to contact the interior surface, e.g., an intima, of the body lumen. The balloon 112 may be maintained at a specified size by pushing the cooling fluid 208 through and/or pulling cooling fluid 208 out of the balloon 112 at a specified flow rate. In certain embodiments, the transducer 111 may be used to output an acoustic signal when the balloon 112 fully occludes a body lumen of a target vessel 210. The balloon 112 may center the transducer 111 within the body lumen. In certain embodiments, e.g., suitable for renal denervation, the balloon 112 is inflated while inserted in the body lumen of the patient during a procedure at a working pressure of about 10 to about 30 psi using the cooling fluid 208. The balloon 112 may be or include a compliant, semi-compliant, or non-compliant medical balloon 112. The balloon 112 is sized for insertion in the body lumen and, in the case of insertion into the renal artery, for example, the balloon 112 may be selected from available sizes including outer diameters of 3.5, 4.2, 5, 6, 7, or 8 mm, but not limited thereto. When activated the transducer 111 can deliver the acoustic signal to a vessel wall 212 of the target vessel 210.

Figure 3:
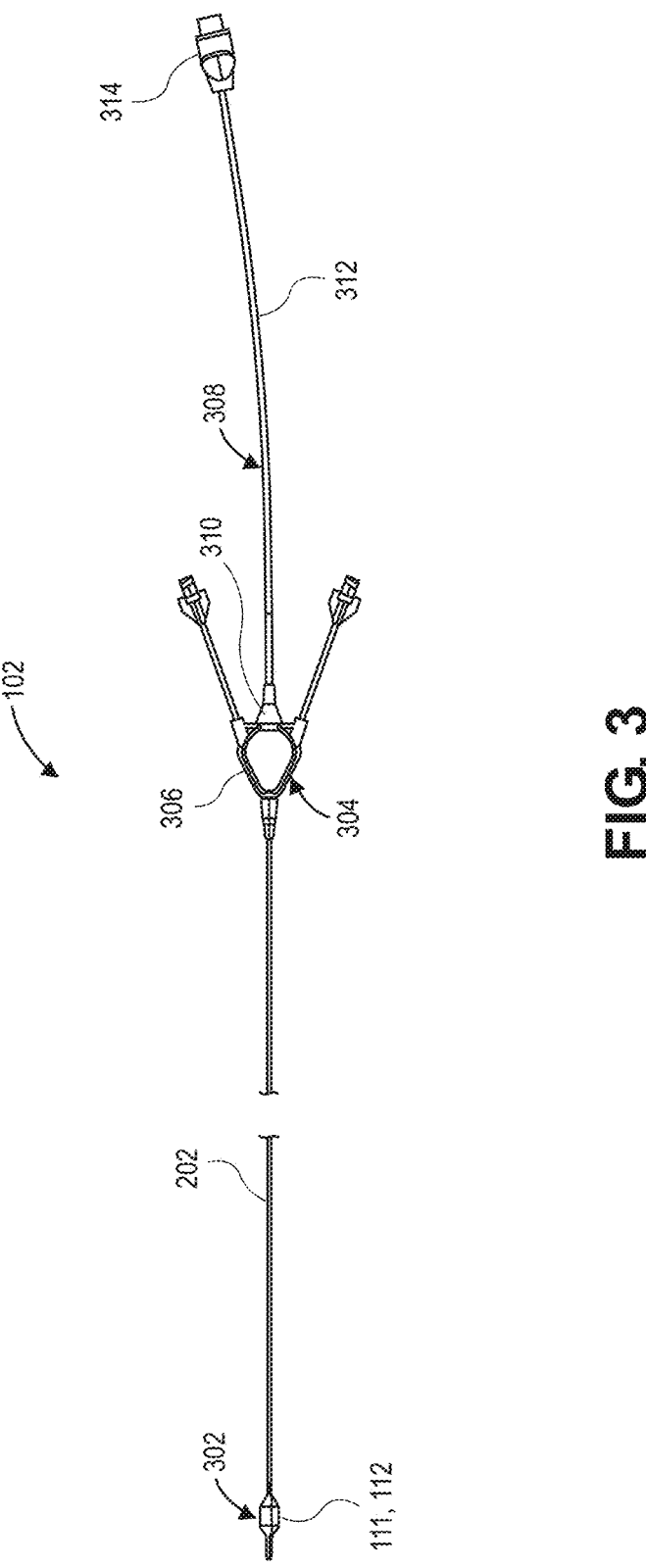
FIG. 3 is a plan view of a tissue treatment catheter, in accordance with an embodiment.

Referring to FIG. 3, a plan view of a tissue treatment catheter is shown in accordance with an embodiment. The tissue treatment catheter 102 can have a modular construction. More particularly, the tissue treatment system 100 may include an assembly composed of several subassemblies. The subassemblies can divide the overall assembly into segments that are manufactured at the subassembly level and then combined to form the full assembly.

The modular construction of the tissue treatment catheter 102 includes a distal catheter subassembly 302. The distal catheter subassembly 302 may include the balloon 112, the ultrasound transducer 111, and an isolation tube (not shown). The modular construction may also include a medial catheter subassembly 304. The medial catheter subassembly 304 may include the catheter shaft 202 and a lumen hub 306. As described below, the lumen hub 306 may include a hub component overmolded on the catheter shaft 202. The hub components can include fluid conduits extending in a wye configuration. The modular construction can include a proximal catheter subassembly 308. The proximal catheter subassembly 308 may include an electrical connector 310 connected to the lumen hub 306, and an extension cable 312 that extends proximally from the lumen hub 306 to a proximal connector 314. Each of the catheter subassemblies is described in further detail below.

Figure 4:
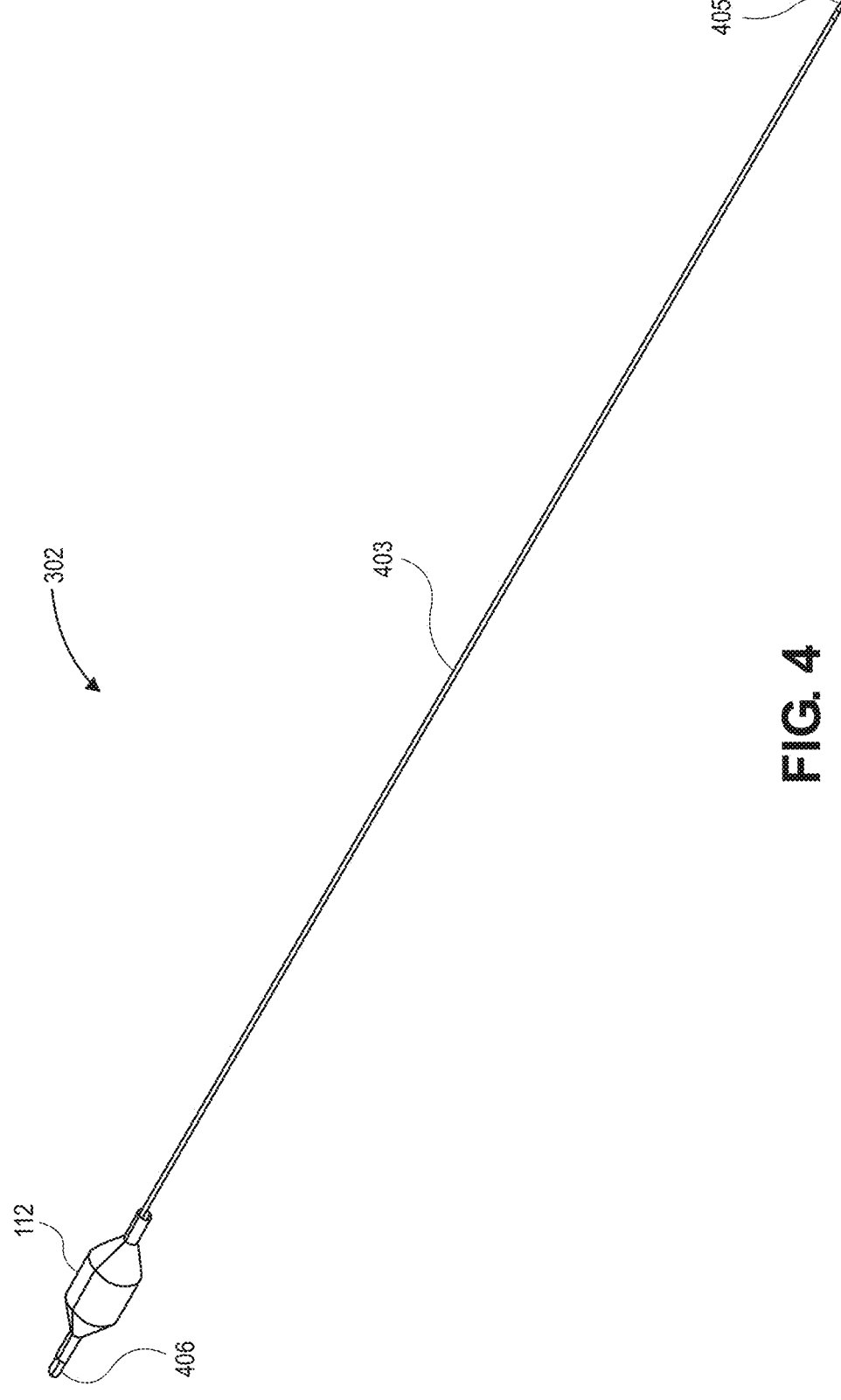
FIG. 4 is a perspective view of a distal catheter subassembly of a tissue treatment catheter, in accordance with an embodiment.

Referring to FIG. 4, a perspective view of a distal catheter subassembly of a tissue treatment catheter is shown in accordance with an embodiment. The distal catheter subassembly 302 can include an isolation tube 403. The isolation tube 403 extends longitudinally in a distal direction from a proximal tube end 405 to the balloon 112. The distal catheter subassembly 302 can include a distal catheter tip 406 of the tissue treatment catheter 102. The isolation tube 403 can extend from the proximal tube end 405 to the distal catheter tip 406. In an embodiment, the balloon 112 is mounted on the distal catheter tip 406. Accordingly, the balloon 112 can contain and surround a distal portion of the isolation tube 403.

Figure 5:
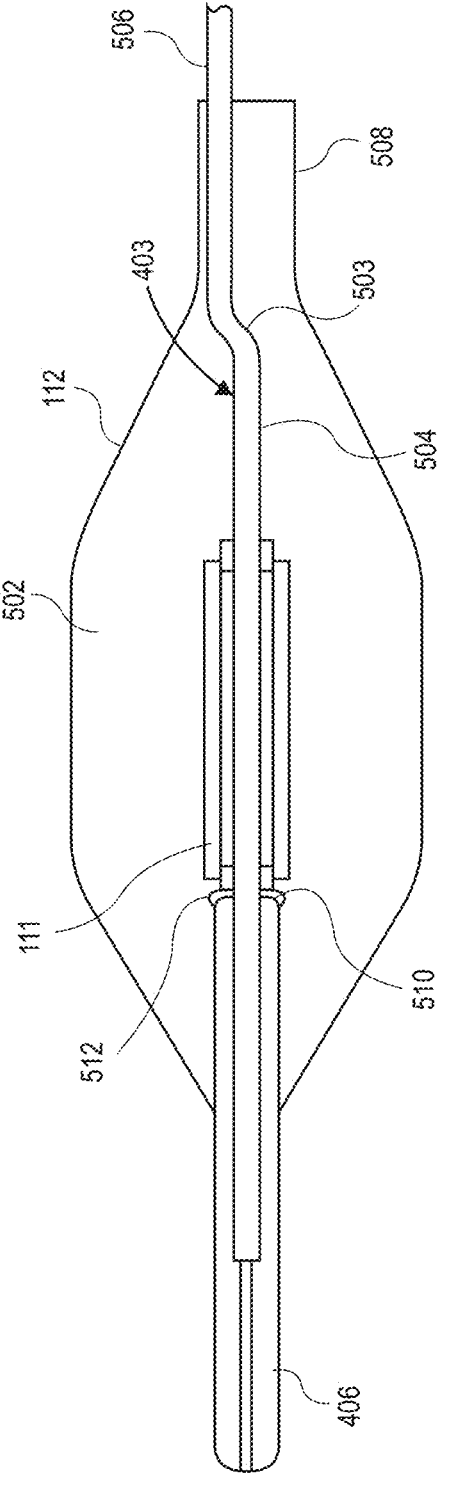
FIG. 5 is a sectional view of a distal catheter subassembly of a tissue treatment catheter, in accordance with an embodiment.

Referring to FIG. 5, a sectional view of a distal catheter subassembly of a tissue treatment catheter is shown in accordance with an embodiment. The isolation tube 403 can extend through an interior 502 of the balloon 112 to the distal catheter tip 406. The interior 502 can be a space within the balloon 112 to receive an inflation fluid, as described below. In an embodiment, the ultrasound transducer 111 is located or disposed in the interior 502. More particularly, the transducer 111 is contained within the interior 502.

The ultrasound transducer 111 may include a cylindrical hollow tube made of a piezoelectric material (e.g., lead zirconate titanate (PZT), etc.). The transducer 111 can include one or more electrodes, e.g., inner and outer electrodes, disposed on inner and outer surfaces of the cylindrical tube, respectively. Such a cylindrical hollow tube of piezoelectric material is an example of, and thus can be referred to as, a piezoelectric transducer body. The piezoelectric transducer body can have various other shapes and need not be hollow. In certain embodiments suitable, e.g., for renal denervation, the piezoelectric material, of which the piezoelectric transducer body is made, is lead zirconate titanate 8 (PZT8), which is also known as Navy III Piezo Material. Raw PZT transducers may be plated with layers of copper, nickel and/or gold to create electrodes on surfaces (e.g., the inner and outer surfaces) of the piezoelectric transducer body. Application of a voltage and alternating current across the inner and outer electrodes causes the piezoelectric material to vibrate transverse to the longitudinal direction of the cylindrical tube and radially emit ultrasonic waves.

In an embodiment, the ultrasound transducer 111 is positioned within the interior 502 of the balloon 112. As described below, the balloon 112 can have the interior 502 in fluid communication with a fluid lumen of the catheter shaft 202, and thus, cooling fluid 208 conveyed into the interior 502 from the fluid lumen can cool the transducer 111 during operation.

The transducer 111 can be mounted on the isolation tube 403. For example, the cylindrical hollow tube of the transducer 111 can have a transducer lumen extending longitudinally from a distal end of the transducer to a proximal end of the transducer, and the isolation tube 403 can extend through the lumen. Accordingly, the isolation tube 403 can extend from the distal catheter tip 406, through the ultrasound transducer 111, to the proximal tube end 405 (FIG. 4).

The isolation tube 403 may extend at least partially through the distal catheter tip 406. A proximal tip end 510 of the distal catheter tip 406 can be proximal to a distal end of the isolation tube 403. In an embodiment, the proximal tip end 510 is adjacent to the transducer 111. More particularly, a gap of less than 5 mm may be present between the transducer 111 and the proximal tip end 510. The adjacency of the components can reduce a likelihood of kinking during catheter delivery. More particularly, the absence of a substantial stiffness transition between the transducer 111 and the distal catheter tip 406 can reduce a likelihood of bending when being tracked through tortuous anatomy. The stiffness transition may be further blended by filling the gap between the components with a filling adhesive 512. The filling adhesive 512 may include an ultraviolet-activated medical adhesive, an epoxy, etc. In any case, the filling adhesive 512 can eliminate any gap or space longitudinally between the transducer 111 and the distal catheter tip 406 to provide a uniform stiffness profile that resists kinking.

In an embodiment, the isolation tube 403 includes a jog 503. The jog 503 can include a brief bend or change in direction. The jog 503 can be a portion of the isolation tube 403 that interconnects a distal isolation tube segment 504 with a proximal isolation tube segment 506. The isolation tube segments can extend longitudinally, however, the jog 503 can have a transverse component. Accordingly longitudinal axes of the distal isolation tube segment 504 and the proximal isolation tube segment 506 may be transversely offset from each other.

Figure 25:
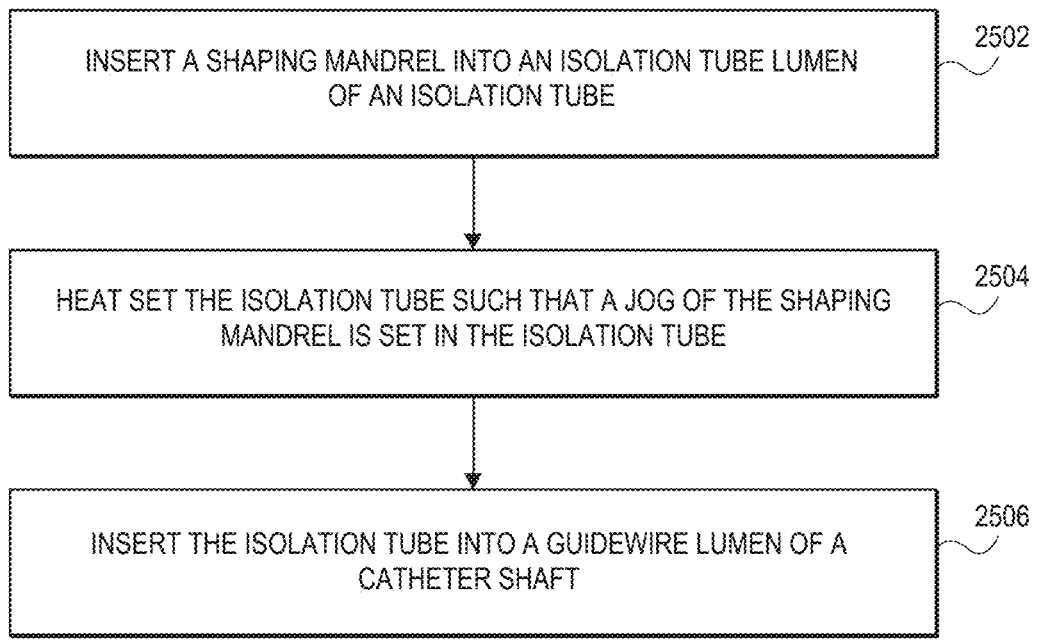
FIG. 25 is a flowchart of a method of manufacturing a distal catheter subassembly of a tissue treatment catheter, in accordance with an embodiment.

The jog 503 can be a bend in the isolation tube 403 that exists even in the absence of an external load. More particularly, the jog 503 can be part of the isolation tube structure, present in the distal catheter subassembly 302, rather than a deformation of the structure caused by external loading. In an embodiment, the jog 503 is heat set in the isolation tube 403 through a heat setting process. For example, referring to FIG. 25, a method of manufacturing a distal catheter subassembly 302 having an isolation tube 403 including the jog 503 is shown in accordance with an embodiment. At operation 2502, a shaping mandrel is inserted into the isolation tube 403. The shaping mandrel can be a mandrel that includes a jog or a bend, referred to as a mandrel jog. The mandrel can be formed from a stiffer material than the isolation tube 403 and, thus, the isolation tube 403 can bend into a shape of the mandrel jog when the mandrel is located within the isolation tube lumen.

The isolation tube 403 can include a core tube, or layer. More particularly, the core tube may be formed from polyimide. The core tube may therefore include a polyimide tubing. In an embodiment, the isolation tube 403 includes a tie layer. For example, the tie layer can include a urethane coating layered over an outer surface of the core tube. The urethane coating can enhance the strength of the polyimide tubing. Furthermore, the tie layer may act essentially as a primer layer to facilitate bonding of the isolation tube 403 to the catheter shaft 202. For example, an adhesive used to form an adhesive joint between the isolation tube 403 and the catheter shaft 202 can preferentially bond to the tie layer, as compared to the core tube.

At operation 2504, during fabrication of the isolation tube 403, when the shaping mandrel having the bend is inserted into the isolation tube 403, the isolation tube 403 can be heat set. The heat setting process may be used to thermally form the jog 503 in the isolation tube 403. For example, the isolation tube 403 can be heat set such that the jog 503 is set in one or more of the core tube or the tie layer. The jog 503 may therefore be a permanent feature of the isolation tube 403 that offsets the axes of the distal isolation tube segment 504 and the proximal isolation tube segment 506.

Notably, the jog 503 can be within the interior 502 of the balloon 112. For example, the jog 503 may be longitudinally between the transducer 111 and a mounting neck 508 of the balloon 112. The mounting neck 508 can be a cylindrical wall portion of the balloon, e.g., proximal to a working section of the balloon, and can have a smaller diameter than the working section. Accordingly, the mounting neck 508 can be mounted on the catheter shaft 202, as described below, to assemble the distal catheter subassembly 302 to the medial catheter subassembly 304. Accordingly, the jog 503 may be longitudinally between the transducer 111 and the catheter shaft 202.

A thickness of the tie layer can influence the heat setting of the isolation tube 403. In an embodiment, the heat setting process primarily causes heat setting of the tie layer, as compared to the core layer. The tie layer can include a urethane coating having a thickness in a range of 5-15 microns, e.g., 10 microns. Such thickness can take on a heat set when heated several times in a heat setting die, e.g., at a temperature of 340+/−5 degrees Fahrenheit for two cycles of 10 seconds each. The heat set of the tie layer can be sufficient to maintain the core tube in the jog shape also. The isolation tube 403 can therefore be heat set to take on the mandrel shape prior to being inserted into the catheter shaft 202.

At operation 2506, the isolation tube 403 can be inserted into a guidewire lumen of the catheter shaft 202. The shaping mandrel can be removed, before or after insertion of the isolation tube 403. In any case, the axes of the catheter shaft 202 and the isolation tube 403 can be radially offset from each other, within the catheter shaft 202. Accordingly, the isolation tube jog 503 can be located within the catheter shaft 202, as shown and described below with respect to FIG. 15.

Figure 6:
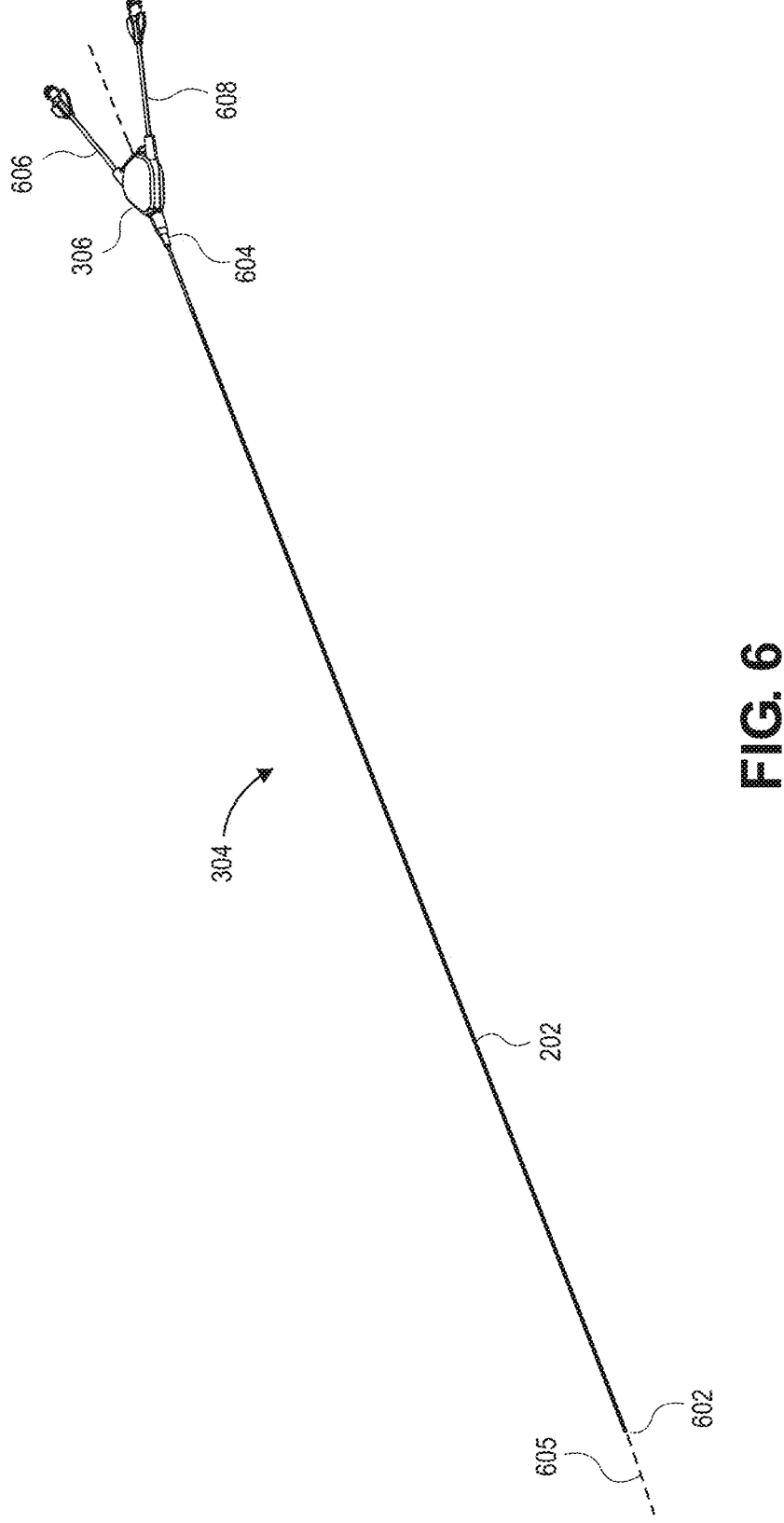
FIG. 6 is a perspective view of a medial catheter subassembly of a tissue treatment catheter, in accordance with an embodiment.

Referring to FIG. 6, a perspective view of a medial catheter subassembly of a tissue treatment catheter is shown in accordance with an embodiment. The medial catheter subassembly 304 can include the catheter shaft 202. The catheter shaft 202 can extend from a distal shaft end 602 to a proximal shaft end 604 along a central axis 605.

The medial catheter subassembly 304 includes the lumen hub 306 mounted on the catheter shaft 202. More particularly, the lumen hub 306 can include a strain relief that is mounted on the proximal shaft end 604 of the catheter shaft 202. The medial catheter subassembly 304 can also include fluid tubes, e.g., a first fluid tube 606 and a second fluid tube 608, connected to the lumen hub 306 and extending transversely outward from the hub relative to a longitudinal axis of the catheter shaft 202, e.g., the central axis 605. The fluid tubes can extend in a wye configuration, symmetrically disposed on opposite sides of the central axis 605.

The medial catheter subassembly 304 may include one or more wires, cables, filaments, or other components not shown in FIG. 6, but described in more detail below. For example, the medial catheter subassembly 304 can include electrical cables extending through the catheter shaft 202. Electrical cables can be connected to the transducer 111 when the distal catheter subassembly 302 and the medial catheter subassembly 304 are combined.

Figure 7:
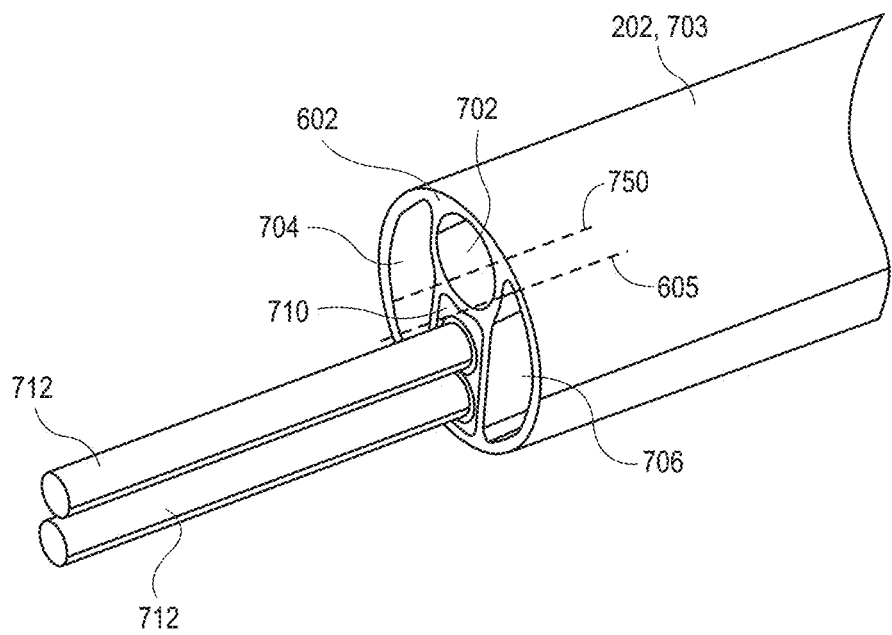
FIG. 7 is a perspective view of a distal shaft end of a catheter shaft of a tissue treatment catheter, in accordance with an embodiment.

Referring to FIG. 7, a perspective view of a distal shaft end of a catheter shaft of a tissue treatment catheter is shown in accordance with an embodiment. The catheter shaft 202, which extends along the central axis 605 to the distal shaft end 602 can include several lumens. In an embodiment, the catheter shaft 202 has a guidewire lumen 702 to allow the tissue treatment catheter 102 to be tracked over a guidewire 207 to a target anatomy. The guidewire lumen 702 can have a circular cross-section profile to conform to a cylindrical outer surface of the guidewire. The guidewire lumen 702 may be radially offset from the central axis 605 of the catheter shaft 202. More particularly, the guidewire lumen 702, which can extend longitudinally through the catheter shaft 202, can have a guidewire lumen axis 750 that is not coaxial with the central axis 605 of the catheter shaft 202. Accordingly, the guidewire lumen 702 may be eccentric relative to a cylindrical outer surface of a sidewall 703 of the catheter shaft 202.

The catheter shaft 202 can include one or more additional lumens located around the guidewire lumen 702. In an embodiment, the catheter shaft 202 includes one or more fluid lumens. The fluid lumens can have semi-circular (or non-circular) cross-sectional profiles to efficiently utilize the available space of the catheter shaft 202. A first fluid lumen 704 can be located on a first side of the catheter shaft 202, and a second fluid lumen 706 may be located on an opposite side of the catheter shaft 202. More particularly, a central plane can be defined by the guidewire lumen axis 750 and the central axis 605. The central plane can contain the guidewire lumen axis 750 and the central axis 605, forming a vertically oriented plane that extends along a length of the catheter shaft 202. The first fluid lumen 704 may be on a first side of the central plane, and the second fluid lumen 706 can be on a second side of the central plane opposite of the first fluid lumen 704. The first fluid lumen 704 and the second fluid lumen 706 can communicate fluid between the controller 120 and the balloon 112. More particularly, the interior 502 of the balloon 112 can be in fluid communication with the fluid lumen(s) when the distal catheter subassembly 302 is assembled to the medial catheter subassembly 304. When combined, a cooling fluid 208 can be communicated through the fluid lumens of the medial catheter subassembly 304 to circulate fluid through the interior 502 of the balloon 112 of the distal catheter subassembly 302. Cooling fluid 208 can be flowed distally through the first fluid lumen 704 and returned proximally through the second fluid lumen 706.

The catheter shaft 202 can include a cable lumen 710 extending longitudinally from the proximal shaft end 604 to the distal shaft end 602. The cable lumen 710 may have a rectangular cross-sectional profile. The cable lumen 710 may be located below the guidewire lumen 702 and between the first fluid lumen 704 and the second fluid lumen 706. The central plane may therefore pass vertically through the cable lumen 710 and the guidewire lumen 702, horizontally between the first fluid lumen 704 from the second fluid lumen 706. In an embodiment, one or more electrical cable 712 is received within the cable lumen 710. The electrical cable(s) 712 can extend through the cable lumen 710 from a proximal connection point within the lumen hub 306 to a distal termination point distal to the distal shaft end 602. Accordingly, the electrical cable 712 can deliver energy from the controller 120, which connects to the electrical cable 712 through the proximal catheter subassembly 308 as described below, to the ultrasound transducer 111. The proximal catheter subassembly 308 can attach to the electrical cable 712 when the catheter subassemblies are combined.

Figure 8:
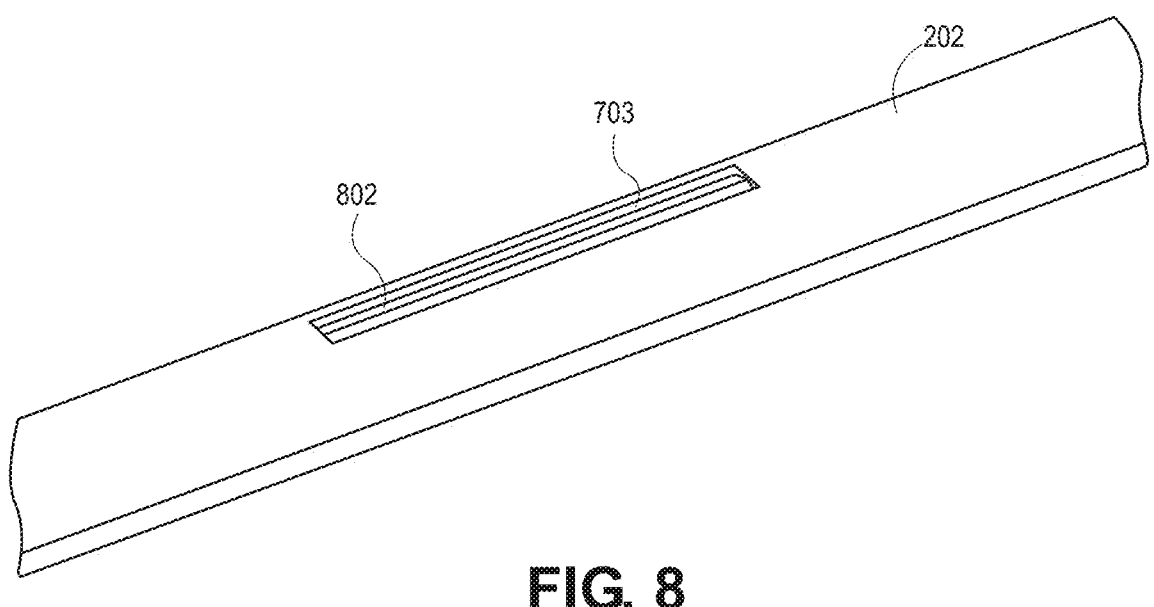
FIG. 8 is a perspective view of a guidewire port of a tissue treatment catheter, in accordance with an embodiment.

Referring to FIG. 8, a perspective view of a guidewire port of a tissue treatment catheter is shown in accordance with an embodiment. The catheter shaft 202 can include a guidewire port 802. The guidewire lumen 702 can extend from the distal shaft end 602 to the guidewire port 802. More particularly, the guidewire port 802 can extend through the sidewall 703 of the catheter shaft 202 into the guidewire lumen 702. For example, the guidewire port 802 can be a hole, cut, slit, skive, etc. formed in the sidewall 703. The port therefore places the guidewire lumen 702 in fluid communication with a surrounding environment, and thus, allows a guidewire 207 to pass through the sidewall 703 from the guidewire lumen 702 to the surrounding environment. Accordingly, the guidewire port 802 can provide a RX port acting as an exit hole formed in the sidewall 703 of the catheter shaft 202 to allow the guidewire 207 to track through a portion of the catheter shaft 202. More particularly, the tissue treatment catheter 102 can be tracked over a guidewire 207 in a RX fashion.

Figure 9:
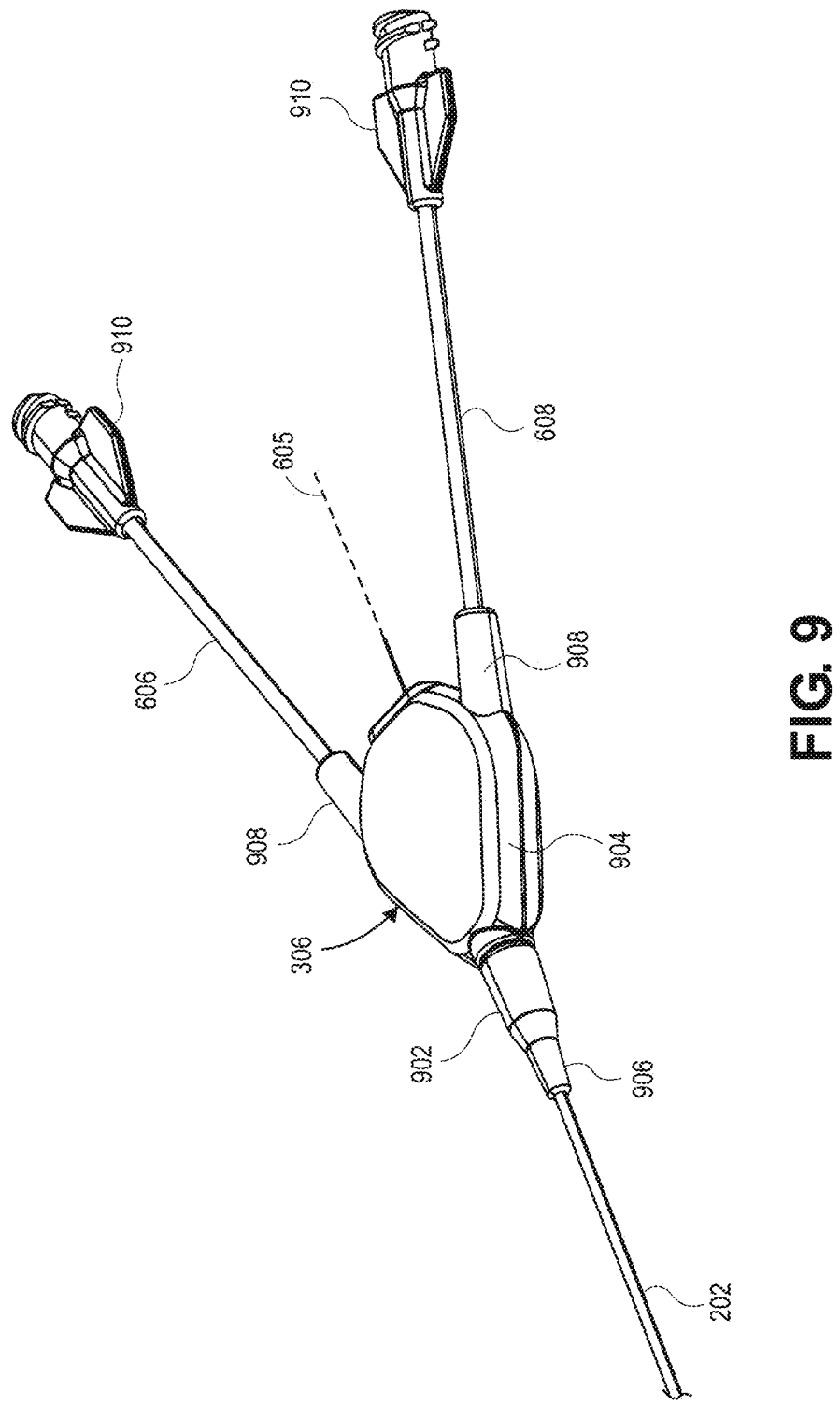
FIG. 9 is a perspective view of a lumen hub of a tissue treatment catheter, in accordance with an embodiment.

Referring to FIG. 9, a perspective view of a lumen hub of a tissue treatment catheter is shown in accordance with an embodiment. The lumen hub 306 can have a symmetric configuration. Inflow and outflow fluid lumens, e.g., the first fluid tube 606 and the second fluid tube 608, can extend laterally outward from the central axis 605 of the catheter shaft 202 in a wye configuration. The symmetric configuration of the fluid lumens can provide ease of use because fluid lumens from the controller 120 can be more easily connected to the fluid connectors 910 on opposite sides of the central axis 605. As described above, the lumen hub 306 can be part of the medial subassembly that is joined to the distal subassembly during manufacturing.

The lumen hub 306 can include an innermold 902 that is partially surrounded by a hub shell 904. The innermold 902 can include several strain reliefs at locations where the lumen hub 306 connects to adjacent structures. For example, the lumen hub 306 can have a distal strain relief 906 attached to the catheter shaft 202, e.g., at the proximal shaft end 604. The lumen hub 306 may also include strain reliefs in a proximal region. For example, proximal strain reliefs 908 can connect to the fluid tubes that extend from the lumen hub 306 in the wye configuration.

Each fluid tube of the medial catheter subassembly 304 may extend proximally to respective fluid connectors 910. The fluid connectors 910 may be connectors that receive and/or attach to a respective fluid transfer device. For example, the fluid connectors 910 may be luer connectors to receive and connect to fluid fittings of the controller 120. Fluid may therefore be communicated through the fluid tubes from the controller 120 to the balloon 112. More particularly, the fluid tubes can be in fluid communication with the fluid lumens of the catheter shaft 202 to transfer fluid between the controller 120 and the balloon 112.

Figure 10:
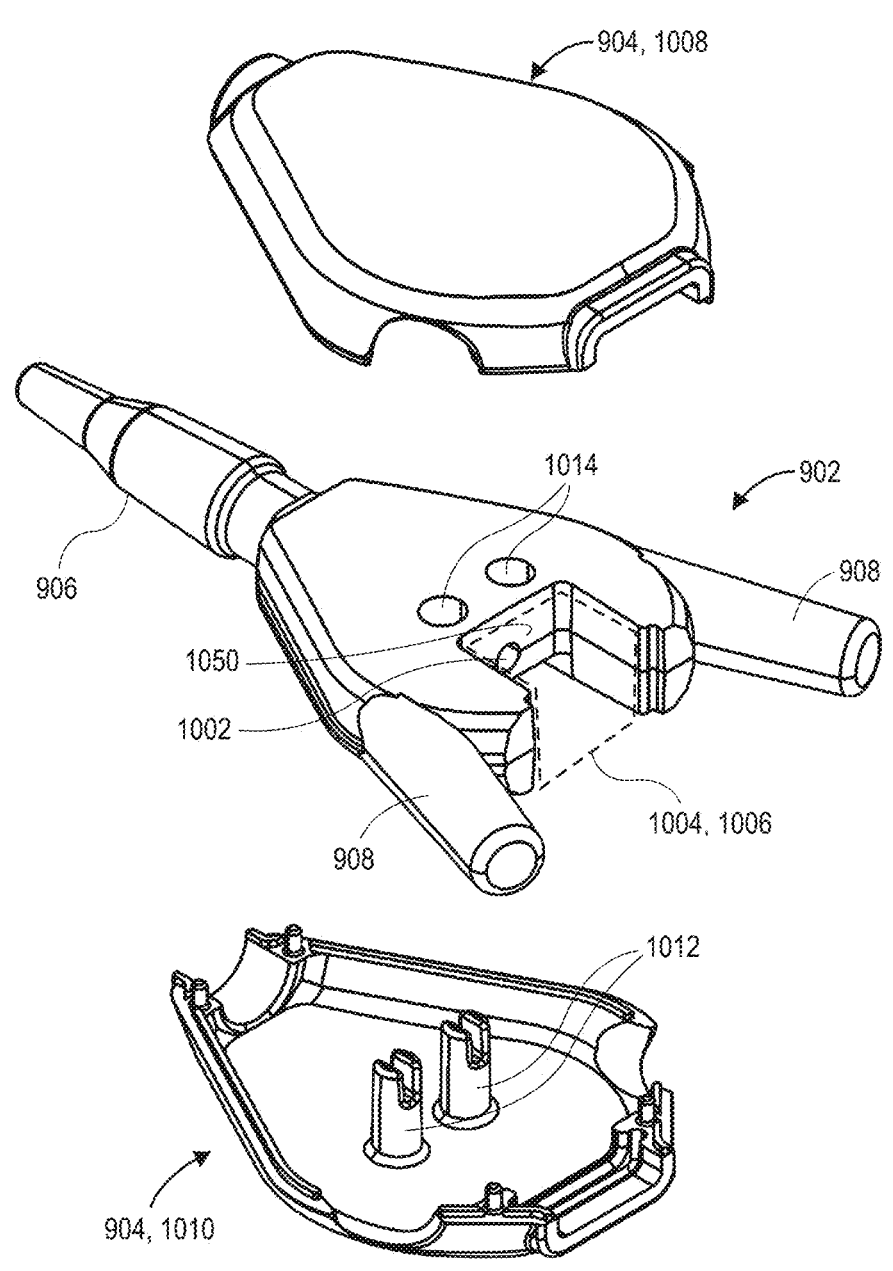
FIG. 10 is an exploded view of a lumen hub of a tissue treatment catheter, in accordance with an embodiment.

Referring to FIG. 10, an exploded view of a lumen hub of a tissue treatment catheter is shown in accordance with an embodiment. The exploded view reveals that the innermold 902 can be a monolithically formed body having various features including the distal strain relief 906 and the proximal strain reliefs 908. Each of the strain reliefs can have respective lumens to receive respective tubular structures. For example, the distal strain relief 906 can receive and contain the proximal shaft end 604 of the catheter shaft 202, and the proximal strain reliefs 908 can contain distal ends of the first fluid tube 606 and the second fluid tube 608. Channels can extend through the innermold 902 to interconnect the strain relief lumens such that the lumens passing through the fluid tubes can be in fluid communication with the fluid lumens passing through the catheter shaft 202.

In certain embodiments, the innermold 902 can also include a central cable channel 1002 extending longitudinally through the distal strain relief 906 and exiting the innermold 902 at a proximal face 1050 of the innermold 902. The catheter shaft 202 can be received within the distal strain relief 906, and the central axis 605 of the catheter shaft 202 can extend through the central cable channel 1002. Furthermore, the central cable channel 1002 can be in communication with the cable lumen 710 of the catheter shaft 202. Accordingly, electrical cables 712 can extend longitudinally through the catheter shaft 202 and the innermold 902 to a location proximal to the innermold 902.

In an embodiment, the region proximal to the innermold 902, into which the electrical cables 712 can extend, includes a proximal notch 1004. The proximal notch 1004 can be a cutout in the innermold 902 sized and shaped to receive a strain relief of the proximal catheter subassembly 308. The cutout can have a U-shaped profile, as shown. The proximal notch 1004 of the innermold 902 can be between the first fluid tube 606 and the second fluid tube 608 when the tubes are inserted into the proximal strain reliefs 908. As described below, the proximal notch 1004 provides a receiving cavity 1006 contained within the proximal notch 1004 between the upper and lower hub shell components. More particularly, when the hub shell 904 is clamped onto and surrounds the innermold 902, the space between the hub shell 904 and within the proximal notch 1004 forms a receiving cavity 1006 to receive the proximal catheter subassembly 308.

The hub shell 904 can include several components that are assembled to each other around the innermold 902. For example, the hub shell 904 can include a first hub shell 1008, shown above the innermold 902, and a second hub shell 1010, shown below the innermold 902. The hub shell components can be attached and/or bonded to each other to form an outer housing surrounding the innermold 902. The hub shell 904 may be formed from a stiffer material, e.g., polycarbonate, than the innermold 902. For example, the innermold 902 may be formed from an injection molded elastomer or similarly soft durometer material. Accordingly, the innermold 902 may be flexible to allow the catheter shaft 202 and the fluid tubes to easily flex, and the hub shell 904 can provide rigidity to support the body of the innermold 902.

In an embodiment, the hub shell 904 includes one or more posts 1012 extending orthogonal to an inner wall of the hub shell 904. The posts 1012 can extend upward to pass through corresponding post holes 1014 in the body of the innermold 902 when the hub shell 904 is assembled onto the innermold 902. The posts 1012 can engage mating components (not shown) of the hub shell 904 to secure a first half of the hub shell to a second half of the hub shell. For example, the posts 1012 can engage and connect to corresponding clips or tubes in the adjacent hub shell component. When engaged, the structural components can hold the hub shells 904 together around the innermold 902. Furthermore, as described below, the posts 1012 may connect to the tension member to anchor the tension member within the lumen hub 306.

Figures 11, 12:
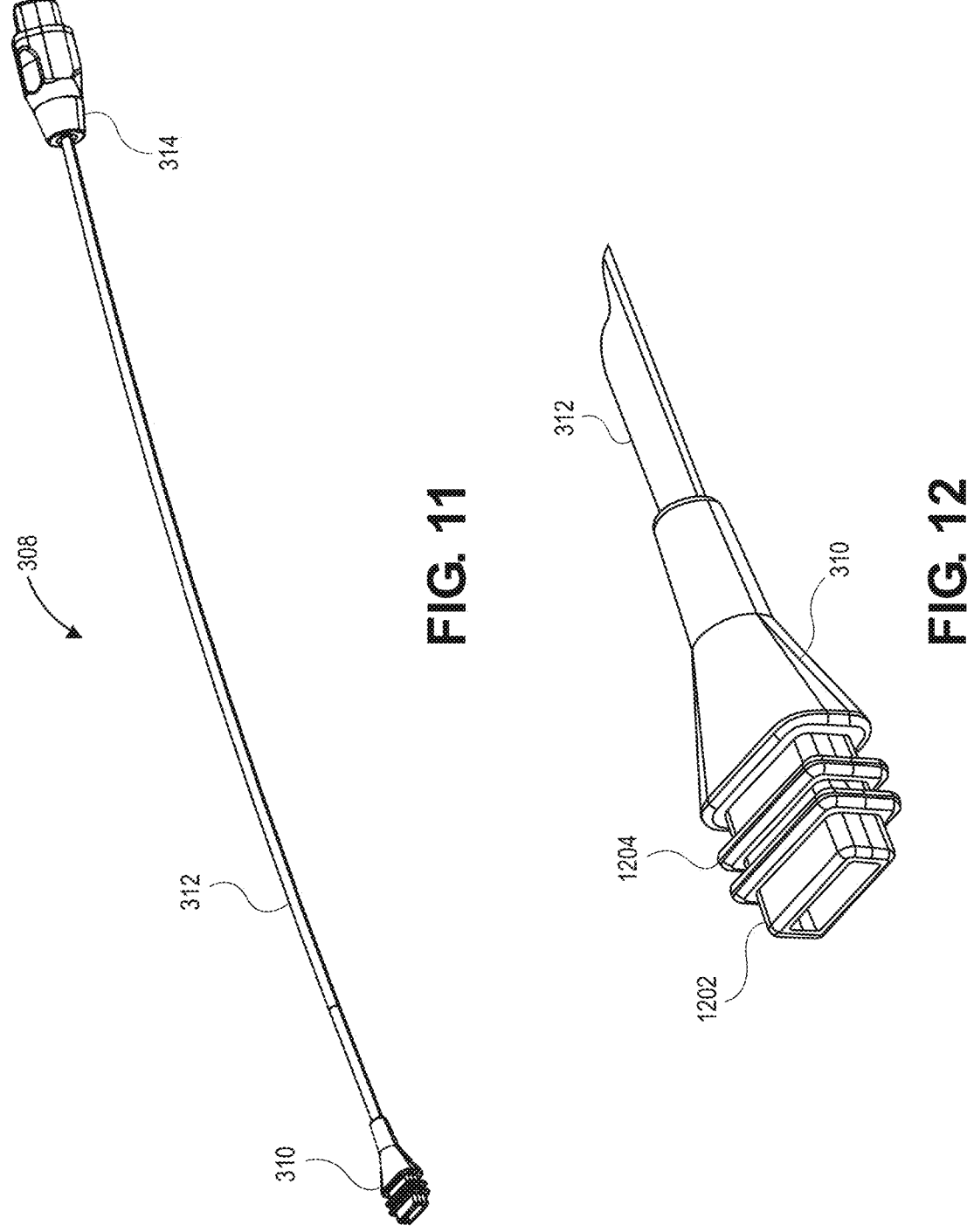
FIG. 11 is a perspective view of a proximal catheter subassembly of a tissue treatment catheter, in accordance with an embodiment.
FIG. 12 is a perspective view of an electrical connector of a tissue treatment catheter, in accordance with an embodiment.

Referring to FIG. 11, a perspective view of a proximal catheter subassembly of a tissue treatment catheter is shown in accordance with an embodiment. The proximal catheter subassembly 308 includes the electrical connector 310 at a distal end, and the proximal connector 314 at a proximal end. The extension cable 312 extends proximally from the electrical connector 310 to the proximal connector 314. The extension cable 312 can be a lightweight and thin cable. Accordingly, the extension cable 312 may not add substantial weight to the proximal end of the catheter. By contrast, the proximal connector 314 can attach to a bulky electrical cable, e.g., the connection cable 140, that then extends to attach to the controller 120. The bulky electrical cable can be quite heavy. The extension cable 312 can separate the catheter shaft 202 from the bulky cable, and therefore the bulky cable may not pull the catheter shaft 202 off of an operating table when the tissue treatment catheter 102 is connected to the bulky cable.

Referring to FIG. 12, a perspective view of an electrical connector of a tissue treatment catheter is shown in accordance with an embodiment. The electrical connector 310 may include a connector housing 1202 at a distal end. The connector housing 1202 can have a tubular, rectangular body to insert into the receiving cavity 1006 of the lumen hub 306. In an embodiment, one or more ridges 1204 can extend peripherally about the connector housing 1202. The ridges 1204 can extend laterally from the connector housing 1202 to engage mating features of the innermold 902, as described below.

Figure 13:
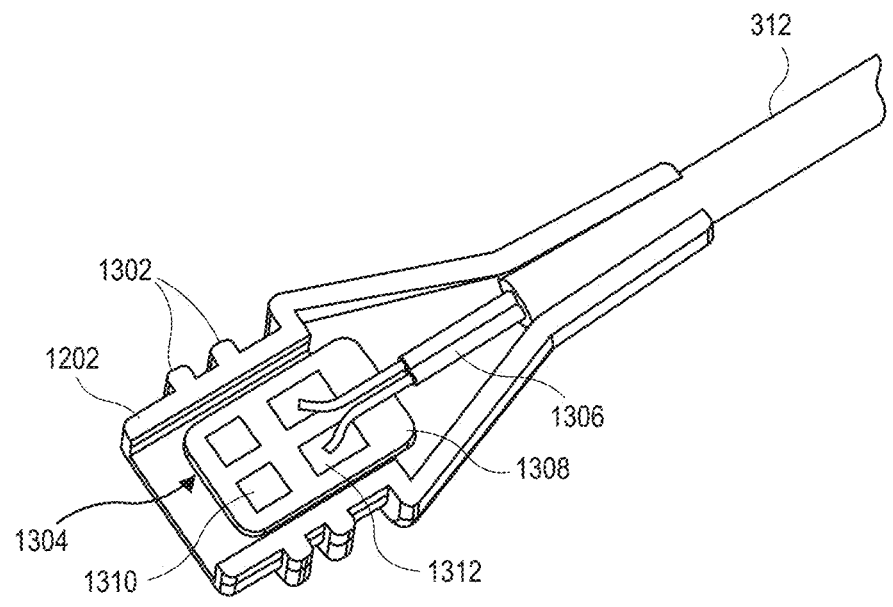
FIG. 13 is a sectional view of an electrical connector of a tissue treatment catheter, in accordance with an embodiment.

Referring to FIG. 13, a sectional view of an electrical connector of a tissue treatment catheter is shown in accordance with an embodiment. The ridges 1204 of the electrical connector 310 can provide respective keys 1302. More particularly, each ridge 1204 can provide a key 1302 that can engage a corresponding slot of the innermold 902, as described below. Accordingly, the ridges 1204 of the electrical connector 310 can secure the electrical connector 310 to the lumen hub 306 when the proximal catheter subassembly 308 is attached to the medial catheter subassembly 304.

In cross-section, a cavity within the connector housing 1202 can be seen. The cavity can contain a mending board 1304. The mending board 1304 within the connector housing 1202 can be an electrical component that provides an electrical interconnect between an extension cable wire 1306 of the proximal catheter subassembly 308 and the electrical cable 712 of the medial catheter subassembly 304. The extension cable wire 1306 can be a twisted wire pair or a coaxial cable, for example. The mending board 1304 can have a printed circuit board construction, including a substrate 1308 and two or more contact pads. More particularly, the mending board 1304 can include a distal electrical contact 1310 deposited on the substrate 1308, and a proximal electrical contacts 1312 deposited on the substrate 1308. The distal and proximal contact pads can be interconnected through vias and/or traces passing through the substrate 1308. Accordingly, the proximal electrical contacts 1312 can be electrically connected to the distal electrical contact 1310. The mending board 1304 may include several pairs of contact pads. Each pair can include a respective proximal pad electrically connected to a respective distal pad. For example, the mending board 1304 can include two pairs of contact pads, as shown.

An electrical connection can be made between the electrical cable 712 of the medial catheter subassembly 304 and a twisted wire pair of the proximal catheter subassembly 308 through the mending board 1304. As shown, the extension cable wire 1306 can extend from the proximal electrical contacts 1312 to the proximal connector 314 of the extension cable 312. Similarly, the electrical cable 712, which extends through the cable lumen 710, can connect to the distal electrical contact 1310. Accordingly, an electrical path from the proximal connector 314 through the mending board 1304 to the transducer 111 can be provided by the interconnected extension cable wires 1306 and electrical cables 712.

At the subassembly level, the extension cable wire 1306 can be attached to the proximal electrical contacts 1312 pad of the mending board 1304. The connected cable can then be sealed, e.g., by adding a sealant layer over the contact pads, to protect the electrical connection. When bonded and sealed in such a manner, the subassembly may then be moved to a next manufacturing site and/or operation. At the next operation, the electrical cable 712 can be bonded to the exposed distal contacts, quickly and conveniently, to combine the subassembly.

Given the above description of the system subassemblies, it will be appreciated that the tissue treatment catheter 102 may be built by assembling the catheter subassemblies to each other. Accordingly, a method of manufacturing the tissue treatment catheter 102 can include several operations at which the subassemblies are engaged, attached, connected, or otherwise interrelated with one another.

Figure 26:
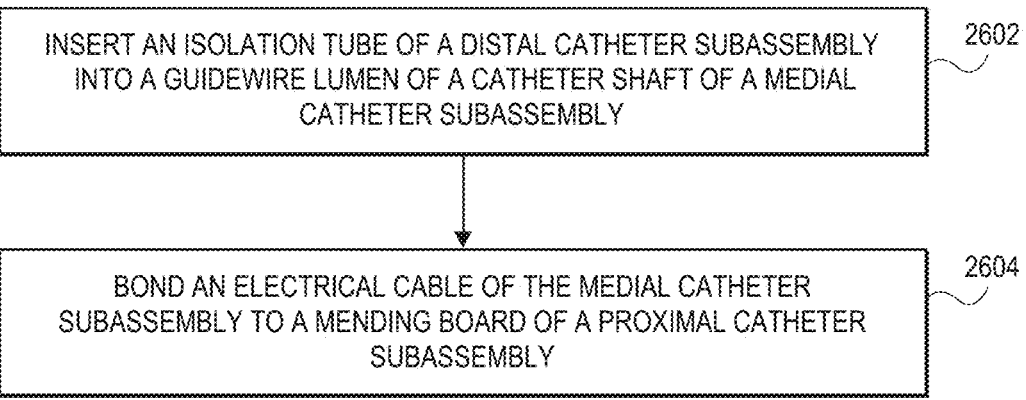
FIG. 26 is a flowchart of a method of manufacturing a tissue treatment catheter, in accordance with an embodiment.

Referring to FIG. 26, operations of a method of manufacturing a tissue treatment catheter are shown. At an operation, the distal catheter subassembly 302 can be assembled to the medial catheter subassembly 304. More particularly, at operation 2602, the isolation tube 403 of the distal catheter subassembly 302 may be inserted into the guidewire lumen 702 of the catheter shaft 202 of the medial catheter subassembly 304. The balloon 112 may be mounted on the catheter shaft 202 such that the interior 502 of the balloon 112 is placed in fluid communication with the fluid lumens of the catheter shaft 202. The balloon 112 and/or the isolation tube 403 can be attached, e.g., bonded, to the catheter shaft 202. Accordingly, the distal catheter subassembly 302 can be combined with the medial catheter subassembly 304.

Figure 22:
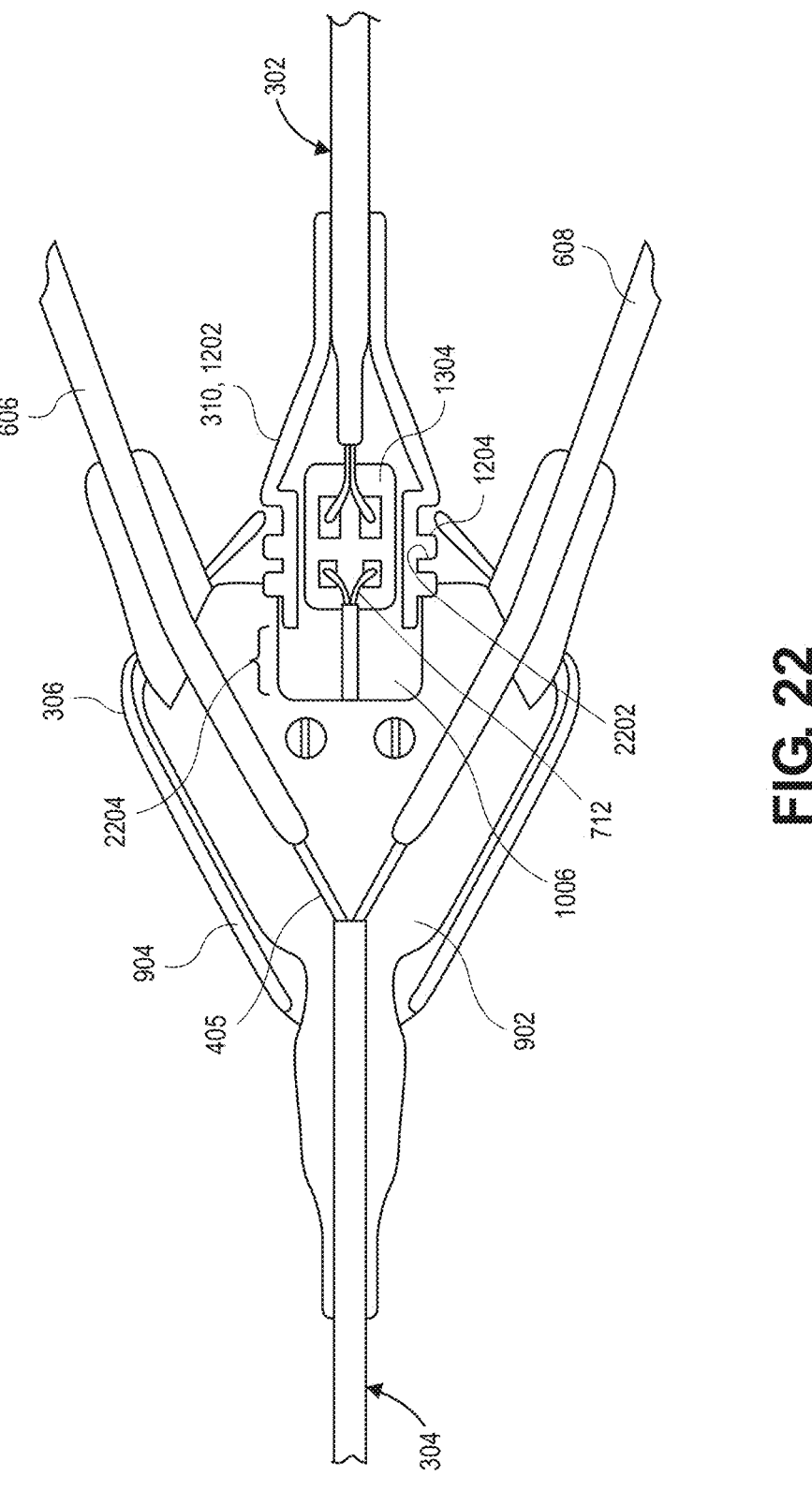
FIG. 22 is a sectional view of a tissue treatment catheter, in accordance with an embodiment.

At an operation, the medial catheter subassembly 304 can be assembled to the proximal catheter subassembly 308. More particularly, at operation 2604, the electrical cable 712 of the medial catheter subassembly 304 can be bonded to the mending board 1304 of the proximal catheter subassembly 308. More particularly, the electrical cable 712 of the medial catheter subassembly 304 can be bonded to the distal electrical contact pads 1310. Through the bond, an electrical connection is made between the proximal electrical connector 310 and the transducer 111. In addition to the mechanical coupling provided by the electrical connector bond, the proximal catheter subassembly 308 may be further connected to the medial catheter subassembly 304 by locating the key 1302 of the connector housing 1202 in a slot of the lumen hub 306 (FIG. 22). Accordingly, the medial catheter subassembly 304 can be combined with the proximal catheter subassembly 308.

When the subassemblies of the modular tissue treatment catheter 102 are assembled to each other, the overall assembly is formed. The catheter assembly includes certain relationships between the subassemblies, which are described further below.

Figure 14:
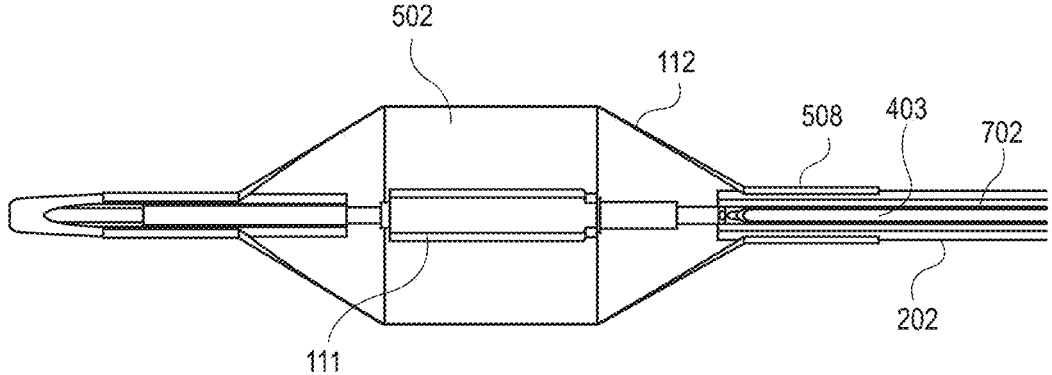
FIG. 14 is a top view of a distal catheter subassembly of a tissue treatment catheter, in accordance with an embodiment.

Referring to FIG. 14, a top view of a distal catheter subassembly of a tissue treatment catheter is shown in accordance with an embodiment. When the isolation tube 403 is inserted into the guidewire lumen 702 of the catheter shaft 202, the balloon 112 can be mounted on the catheter shaft 202. For example, the mounting neck 508 of the balloon 112 can receive the catheter shaft 202 and be bonded to an outer surface, e.g., the sidewall 703, of the catheter shaft 202. Accordingly, the balloon 112 can be secured and sealed to the catheter shaft 202 to place the interior 502 of the balloon 112 in fluid communication with fluid lumens of the catheter shaft 202. The cooling fluid 208 may therefore be circulated through the catheter shaft 202 into the interior 502 to cool the transducer 111 during use.

Figure 15:
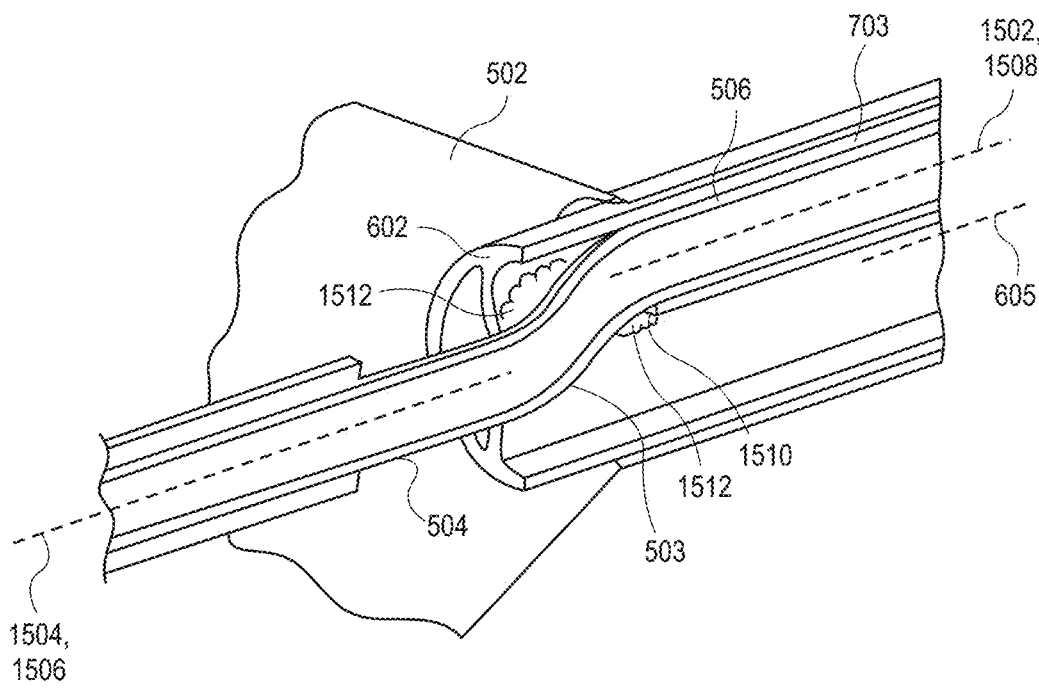
FIG. 15 is a perspective sectional view of a distal catheter subassembly of a tissue treatment catheter, in accordance with an embodiment.

Referring to FIG. 15, a perspective sectional view of a distal catheter subassembly of a tissue treatment catheter is shown in accordance with an embodiment. As described above, the guidewire lumen 702 can be radially offset from the central axis 605 of the catheter shaft 202. More particularly, the guidewire lumen 702 can have a lumen axis 1502, and the lumen axis 1502 may be radially offset from the central axis 605. Similarly, the transducer 111 can have a transducer axis 1504 extending longitudinally through the transducer 111 and the balloon 112.

The isolation tube 403 can have a distal tube axis 1506 extending longitudinally through the distal isolation tube segment 504, and a proximal tube axis 1508 extending longitudinally through the proximal isolation tube segment 506. The distal tube axis 1506 extends distal to the jog 503, and the proximal tube axis 1508 extends proximal to the jog 503. Notably, because the isolation tube 403 is redirected through the jog 503, the distal tube axis 1506 and the proximal tube axis 1508 are not coaxial. Although the isolation tube axes are not coaxial, they can align with the longitudinal axes of other catheter components. More particularly, the proximal tube axis 1508 can be coaxial with the lumen axis 1502 of the guidewire lumen 702, and the distal tube axis 1506 can be coaxial with the transducer axis 1504 of the transducer 111. Furthermore, the transducer axis 1504 can be centered relative to the catheter shaft 202 because of the jog 503. More particularly, the transducer axis 1504 can be coaxially aligned with the central axis 605.

As used herein, "coaxially aligned" encompasses embodiments in which the referred-to axes are not perfectly aligned, but are within a range of radial offset and/or tilt relative to each other. The range of offset allows for the central axis 605 to extend longitudinally through the transducer 111 lumen. More particularly, the jog 503 in the catheter shaft 202 can position the transducer axis 1504 radially inward toward the central axis 605, e.g., closer to the central axis 605 than the lumen axis 1502, and thus, the transducer axis 1504 may be coaxially aligned with the central axis 605. With the transducer 111 shifted toward the central axis 605, away from the lumen axis 1502, the transducer 111 lumen may be centered on the central axis 605 of the catheter shaft 202. For example, the transducer axis 1504 and the central axis 605 may be radially offset from each other by a distance equal to or less than a radius of the guidewire lumen 702. The transducer 111 lumen may therefore be considered centered on the central axis 605 rather than, for example, being centered on the lumen axis 1502. The transducer axis 1504 and the central axis 605 may therefore still be considered coaxially aligned even though the axes are not perfectly aligned. Similarly, the isolation tube 403 can bend slightly between the distal end of the catheter shaft 202 and the ultrasound transducer 111, and thus, the transducer axis 1504 and the central axis 605 of the catheter shaft 202 may tilt slightly relative to each other. Such coaxial alignment nonetheless provides for centering of the ultrasound transducer 111 relative to the catheter shaft 202, and thus, is within the scope of coaxial alignment described herein.

The isolation tube 403 extends through the ultrasound transducer 111 along the transducer axis 1504 and through the guidewire lumen 702 along the lumen axis 1502. Accordingly, proximal to the distal end of the catheter, the isolation tube 403 is radially offset from a central axis 605 of the catheter. The radial offset places the isolation tube 403 closer to an outer wall of the catheter and allows a guidewire 207 to track through the isolation tube 403 to exit through the guidewire port 802, as described below. By contrast, distal to the distal end of the catheter, the isolation tube 403 is centered. It will be understood that, if the isolation tube 403 was not centered, the transducer 111 could be forced to an uncentered location and would therefore tilt relative to an outer surface of the balloon 112. The centered isolation tube 403, however, supports the transducer 111 in a centered, straightened configuration. Thus, energy can be delivered uniformly to the surrounding vessel wall 212 through the balloon 112. Accordingly, the jog 503 allows for the catheter construction to center the transducer 111 within the target anatomy while allowing a RX guidewire design to be utilized.

The jog 503 of the isolation tube 403 can be between the ultrasound transducer 111 and the catheter shaft 202. More particularly, the distal isolation tube portion, which is distal to the jog 503, may be located within the interior 502, distal to the jog 503. Similarly, at least a distal end of the jog 503, at which the jog 503 transitions into the distal isolation tube 403 portion, may be within the interior 502 distal to the distal shaft end 602.

In an embodiment, the catheter shaft 202 includes a notch 1510 to receive the jog 503. The notch 1510 can be at the distal catheter end. For example, the notch 1510 can be cut into the distal catheter end by removing a portion of one or more of the interior shaft walls that divide the several lumens of the catheter shaft 202. The distal ends of the one or more interior shaft walls may therefore be proximal to the distal catheter end. Accordingly, the jog 503 may be recessed into the internal volume of the catheter shaft 202, radially inward from the sidewall 703 of the catheter shaft 202. Locating the jog 503 at least partially within the catheter shaft 202, and distal to the distal ends of the interior shaft wall(s), can structurally support the jog 503 of the isolation tube 403.

In an embodiment, an adhesive joint 1512 may be disposed between the jog 503 and the distal catheter end when the jog 503 is received within the notch 1510. The adhesive joint 1512 can include an adhesive that bonds an inner surface of the catheter shaft 202 defining the guidewire lumen 702 to an outer surface of the isolation tube 403. For example, the adhesive joint 1512 can bond the tie layer of the isolation tube 403 to the catheter shaft 202. The adhesive joint 1512 may include an adhesive filling the guidewire lumen 702 between the jog 503 and the sidewall 703. Similarly, adhesive may be flowed between the jog 503 and the distal ends of the interior walls of the catheter shaft 202. The adhesive joint 1512 can secure and stabilize the isolation tube 403 within the catheter shaft 202.

Figure 16:
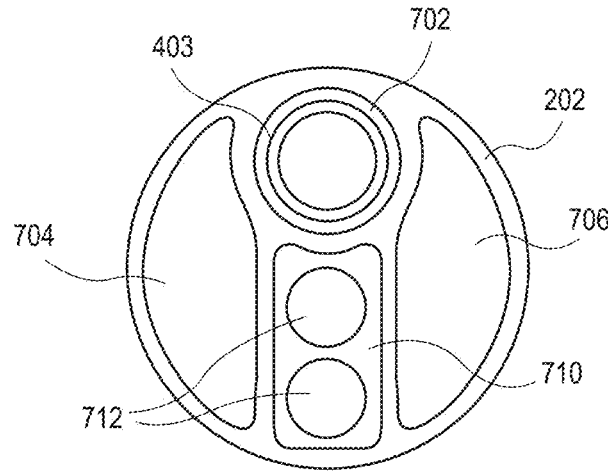
FIG. 16 is a sectional view of a tissue treatment catheter, in accordance with an embodiment.

Referring to FIG. 16, a sectional view of a tissue treatment catheter is shown in accordance with an embodiment. The cross-section can be representative of any cross-section of the catheter shaft 202 taken longitudinally between the jog 503 and the guidewire port 802. The catheter shaft lumens are depicted, including the guidewire lumen 702, the first fluid lumen 704, the second fluid lumen 706, and the cable lumen 710, as described above. The isolation tube 403 is disposed within the guidewire lumen 702. As shown, the isolation tube 403 can have an outer surface that conforms to an inner surface of the guidewire lumen 702. For example, the isolation tube 403 and the guidewire lumen 702 can have matching cylindrical surfaces. By contrast, the electrical cables 712 disposed within the cable lumen 710 may have profiles that are differently shaped than the lumen in which they are located. For example, the electrical cables 712, which extend through the cable lumen 710 to deliver energy to the transducer 111, may have circular profiles, and the cable lumen 710 may have a rectangular profile. It will be appreciated, however, that the illustrated shapes of the lumens and the structures they contain are not intended to be limiting, and may be shaped differently than shown.

Figure 17:
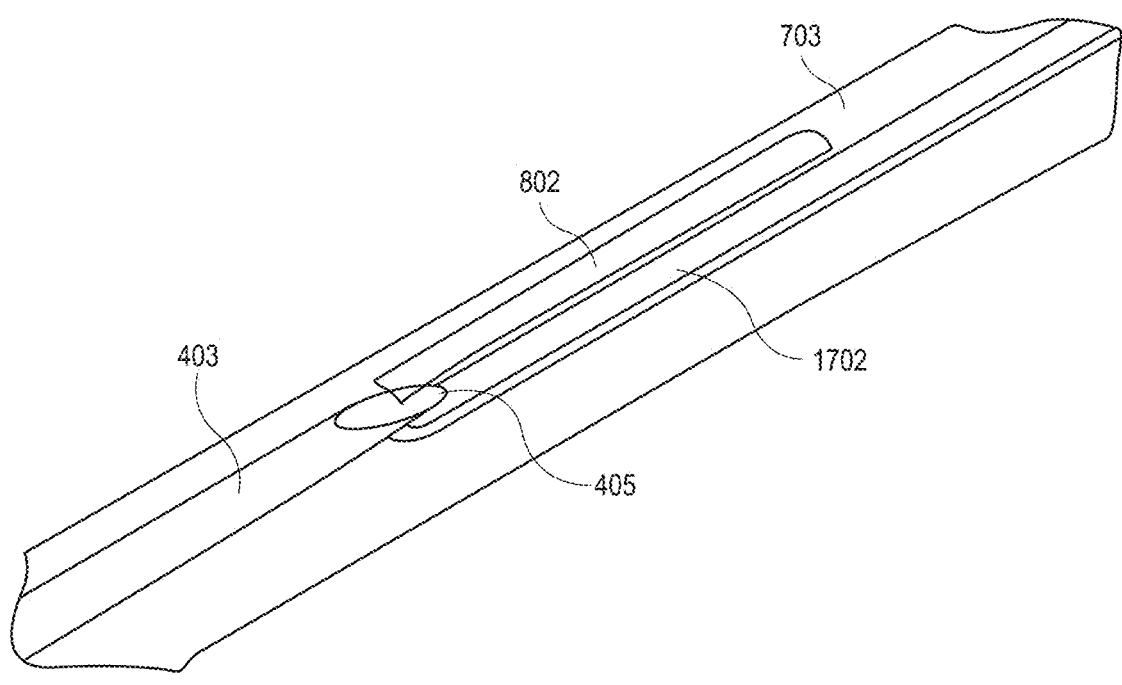
FIG. 17 is a perspective view of a guidewire port of a tissue treatment catheter, in accordance with an embodiment.

Referring to FIG. 17, a perspective view of a guidewire port of a tissue treatment catheter is shown in accordance with an embodiment. As described above, the guidewire port 802 can be an exit hole formed in a sidewall 703 (represented transparently) of the catheter shaft 202. The guidewire port 802 allows the guidewire lumen 702 to provide RX functionality for a guidewire 207. In an embodiment, the isolation tube 403 extends into the guidewire lumen 702 to terminate at the proximal tube end 405. The proximal tube end 405 can be disposed between the distal shaft end 602 and the guidewire port 802. The further the isolation tube 403 extends into the guidewire lumen 702, it has been found, the more support the isolation tube 403 provides to the guidewire 207. Such support can reduce a likelihood of guidewire impingement. Accordingly, the isolation tube 403 may extend into the guidewire lumen 702 such that the proximal tube end 405 of the isolation tube 403 is disposed closer to the guidewire port 802 than the distal shaft end 602. For example, the proximal tube end 405 can be disposed at the guidewire port 802. The isolation tube 403 may therefore extend to the guidewire port 802, e.g., at a location that is 20 cm from the distal shaft end 602. The isolation tube lumen at the proximal tube end 405 can align with the guidewire port 802. Therefore, a guidewire 207 tracking through the isolation tube 403 can exit the isolation tube 403 and immediately pass through the guidewire port 802.

The long isolation tube 403 can provide a guidewire lumen having additional stiffness compared to the guidewire lumen 702. The isolation tube 403 can therefore support the guidewire 207 within the guidewire lumen 702. The additional stiffness and support can, during tracking of the guidewire 207, prevent pinching of the guidewire 207 that would otherwise cause guidewire entrapment.

To support the isolation tube 403 at the guidewire port 802, and to match a stiffness of the catheter shaft 202 distal to the guidewire port 802, a stabilizing member 1702 may be incorporated proximal to the guidewire port 802. The stabilizing member 1702 may, for example, extend through the guidewire lumen 702 proximal to the isolation tube 403. A distal end of the stabilizing member 1702 can be located underneath or just proximal to the proximal tube end 405 of the isolation tube 403. Accordingly, the stabilizing member 1702 can provide stiffness to the catheter body to make the catheter shaft 202 more trackable.

Figure 18:
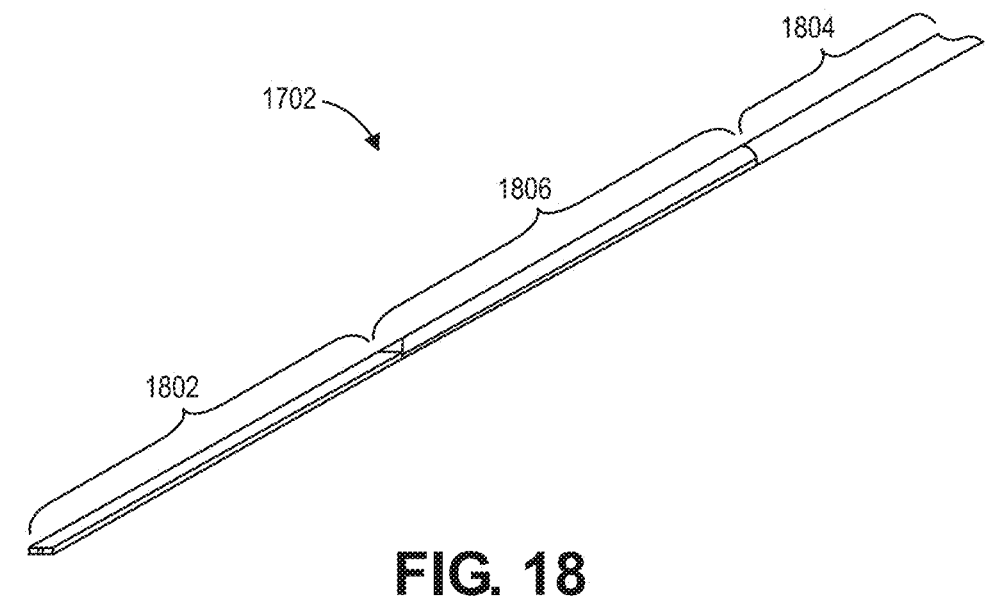
FIG. 18 is a perspective view of a stiffening member of a tissue treatment catheter, in accordance with an embodiment.

Referring to FIG. 18, a perspective view of a stiffening member of a tissue treatment catheter is shown in accordance with an embodiment. The stabilizing member 1702 may include a stylet. The stabilizing member 1702 can be shaped to have different cross-sectional profiles along its length. For example, the stabilizing member 1702 may include a flat distal portion 1802, and a round proximal portion 1804. An intermediate portion 1806 can extend between the flat distal portion 1802 and the round proximal portion 1804 of the stabilizing member 1702. The intermediate portion 1806 can be tapered, and can have a round or rectangular cross-sectional profile along its length.

Figure 19:
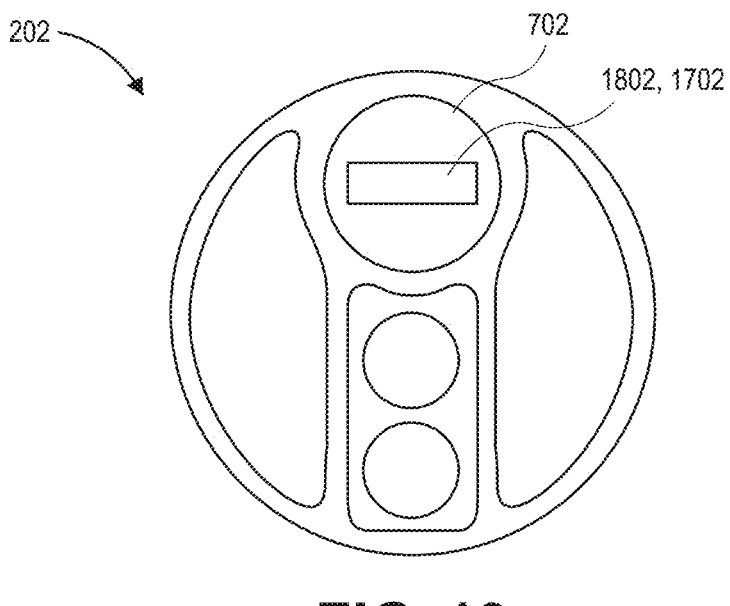
FIG. 19 is a sectional view of a tissue treatment catheter, in accordance with an embodiment.

Referring to FIG. 19, a sectional view of a tissue treatment catheter is shown in accordance with an embodiment. The sectional view illustrates the catheter shaft 202 at a location where the flat distal portion 1802 of the stabilizing member 1702 extends through the guidewire lumen 702. The distal portion can have a rectangular cross-sectional profile. The flattened profile of the stabilizing member 1702 can be achieved during fabrication of the stabilizing member 1702 using, e.g., a grinding, rolling, or coining process. The flattened profile can allow the stabilizing member 1702 to fit between the isolation tube 403 and an inner surface of the guidewire lumen 702 near the central axis 605 of the catheter shaft 202. The distal flattened portion can therefore support the isolation tube 403 and the guidewire 207 running through the isolation tube 403 during catheter tracking. To enhance support of the isolation tube 403, the stabilizing member 1702 may be formed from a stiff material, such as stainless steel.

Figure 20:
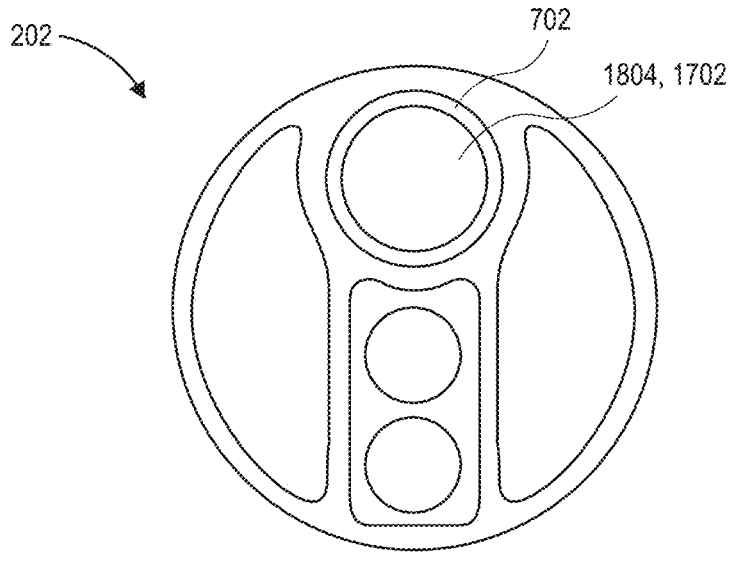
FIG. 20 is a sectional view of a tissue treatment catheter, in accordance with an embodiment.

Referring to FIG. 20, a sectional view of a tissue treatment catheter is shown in accordance with an embodiment. The sectional view illustrates the catheter shaft 202 at a location where the round proximal portion 1804 of the stabilizing member 1702 extends through the guidewire lumen 702. The proximal portion can have a circular cross-sectional profile. The rounded profile can fill and conform to the guidewire lumen 702, similar to the isolation tube 403, to lend stiffness to the catheter shaft 202 proximal to the guidewire port 802. The round proximal portion 1804 can therefore support the catheter shaft 202 and provide a smooth stiffness transition along the shaft length to improve catheter trackability.

Figure 21:
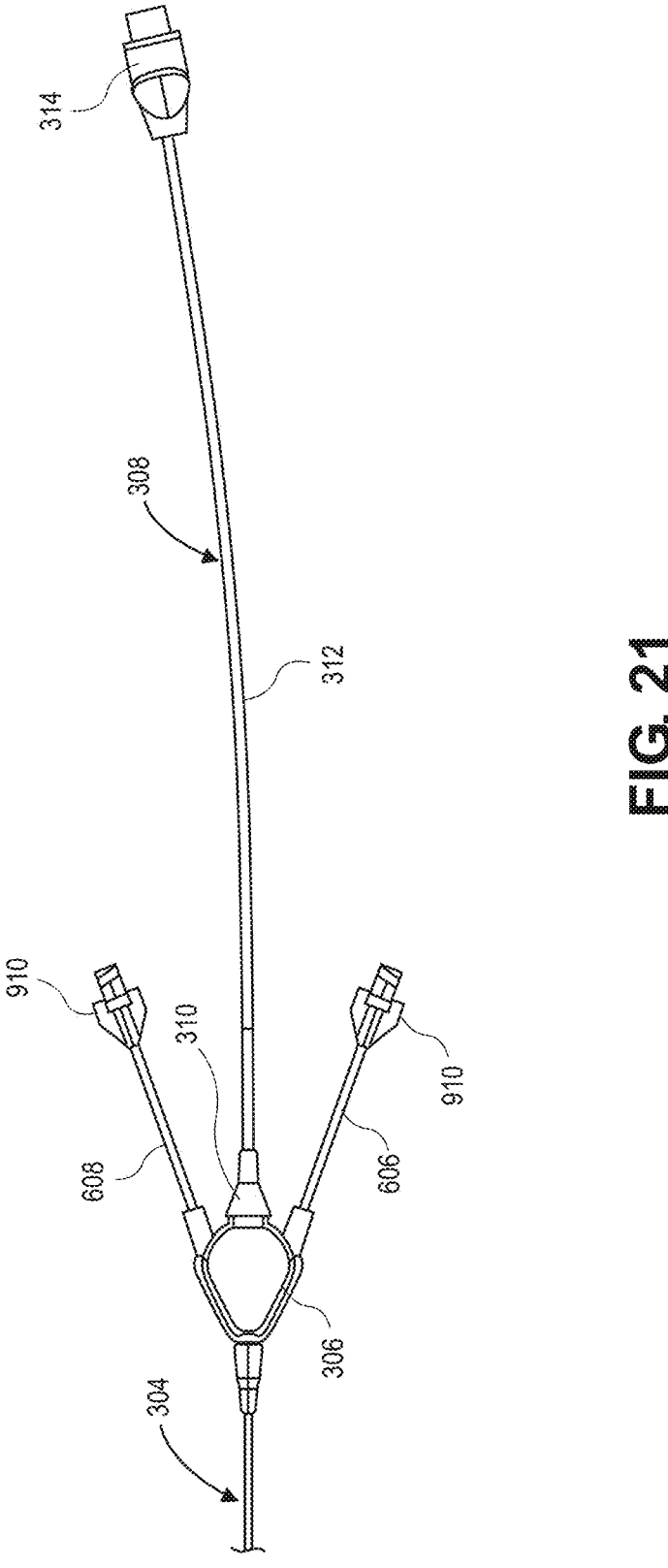
FIG. 21 is a plan view of a tissue treatment catheter, in accordance with an embodiment.

Referring to FIG. 21, a plan view of a tissue treatment catheter is shown in accordance with an embodiment. The proximal catheter subassembly 308 can be connected to the medial catheter subassembly 304. In an embodiment, the electrical connector 310 of the proximal catheter subassembly 308 is inserted into and/or assembled to the lumen hub 306 of the medial catheter subassembly 304. For example, the electrical connector 310 may be connected to the lumen hub 306 radially between the first fluid tube 606 and the second fluid tube 608.

When the proximal catheter subassembly 308 is assembled to the medial catheter subassembly 304, the extension cable 312 can extend proximally, e.g., along the central axis 605, between the fluid tubes of the medial catheter subassembly 304. The extension cable 312 may, for example, be longer than the first fluid tube 606 and the second fluid tube 608. It will be appreciated that the relative locations between the fluid tubes and the extension cable 312, as well as the relative lengths of those components, may provide functional benefits.

With respect to the relative locations, the wye configuration of the fluid tubes provides for the fluid tubes to splay outward in opposite directions from each other. Accordingly, the respective fluid connectors 910 of the fluid tubes may be more easily accessible to connect fittings of the controller 120 to the tissue treatment catheter 102. For example, each fluid tube may splay away from the extension cable 312 to allow a user to easily grip the fluid connector 910 and/or to prevent entanglement of the controller fluid lines, which connect to the fluid tubes 606, 608, and the extension cable 312.

With respect to relative lengths, the longer extension cable 312 can reduce a likelihood of the tissue treatment catheter 102 being pulled off of the operating table. The longer cable may be connected to an external cable of the controller 120 at a point off of, and spaced apart from, the operating table. Spacing the proximal connector 314 apart from the operating table can allow the proximal connector 314 to rest on another surface. The proximal connector 314 may therefore be stabilized, and can allow the lightweight extension cable 312 to hang loosely without substantially loading the tissue treatment catheter 102 and pulling it from the operating table. Furthermore, spacing the proximal connector 314 away from the fluid connectors 910 can make it easier for the user to attach external mating connectors to both the fluid connectors 910 and the proximal connector 314 without the external cables becoming entangled.

Referring to FIG. 22, a sectional view of a tissue treatment catheter is shown in accordance with an embodiment. The electrical connector 310 can be assembled to the lumen hub 306. More particularly, the innermold 902 may include a slot 2202 to receive the ridges 1204 radiating from the connector housing 1202. Accordingly, the electrical connector 310 can fit into the lumen hub 306 and may be secured by a key-and-slot mechanism.

The connector housing 1202 can be received within the receiving cavity 1006 formed between the innermold 902 and the hub shell 904. The inner hub has the U-shaped cutout to receive the connector housing 1202 between the fluid tubes. Accordingly, the lumen hub 306 assembly includes the fluid tubes extending outward in a wye configuration, and the connector housing 1202 located transversely between the fluid tubes along the central axis 605.

In an embodiment, the receiving cavity 1006 is deeper than the portion of the connector housing 1202 that is received therein. More particularly, a longitudinal distance between the innermold face defining a distal boundary of the receiving cavity 1006 and a proximal end of the innermold 902 may be greater than a longitudinal length of the connector housing portion that is inserted into the receiving cavity 1006. Thus, a gap 2204 can be provided between the distal end of the connector housing 1202 and the proximal face of the innermold 902. The gap 2204 can allow the electrical cables 712 that pass distally from the mending board 1304 into the cable lumen 710 of the innermold 902 to flex and bend without binding against an adjacent surface. More particularly, the gap 2204 can create a space within which the cables can deflect as needed to reduce stress on electrical connections when the catheter is being handled.

Figure 23:
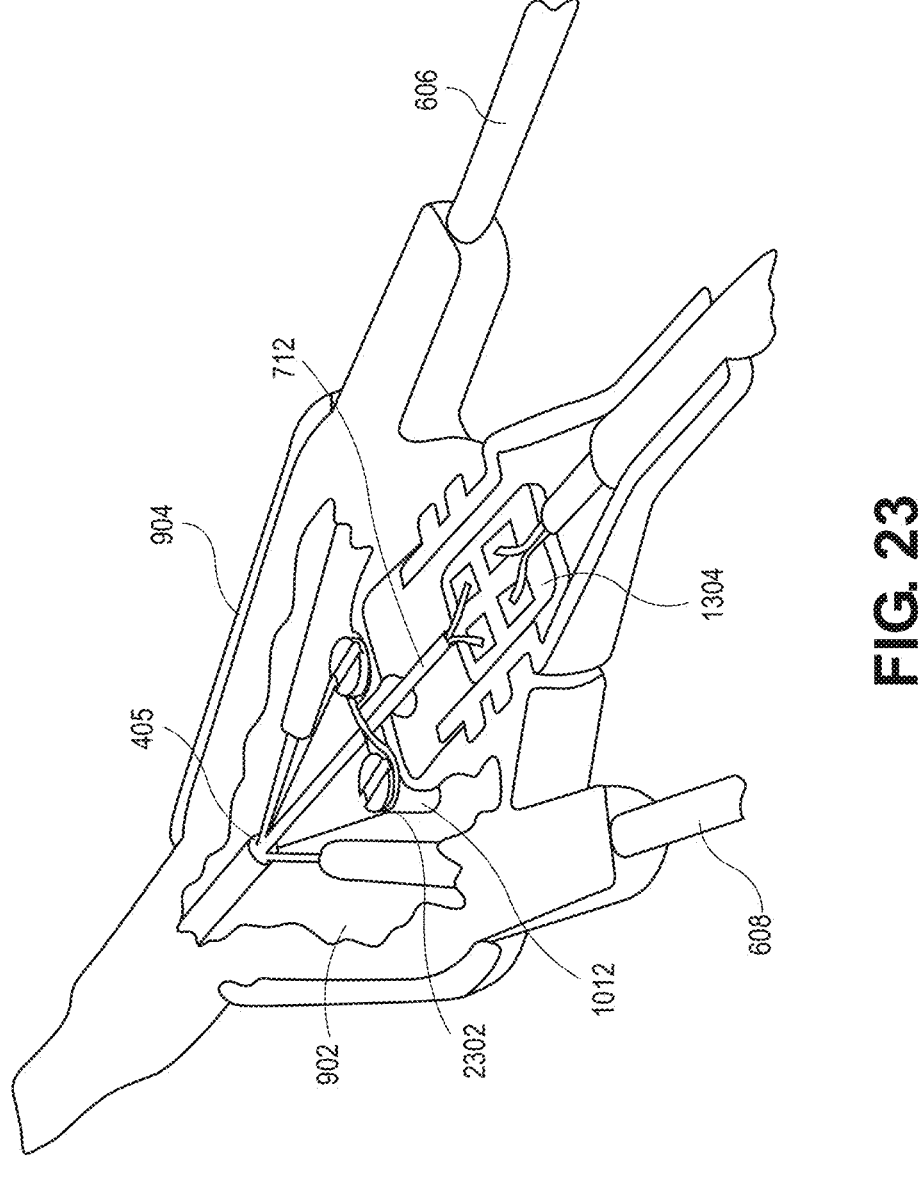
FIG. 23 is a perspective sectional view of a tissue treatment catheter, in accordance with an embodiment.

Referring to FIG. 23, a perspective sectional view of a tissue treatment catheter is shown in accordance with an embodiment. Optionally, in an embodiment, a tension member 2302 can extend through the electrical cable 712. The tension member 2302 may, for example, include a Kevlar cable that extends alongside or wraps around the electrical cables 712. More particularly, the Kevlar cable can extend axially though a wall of sheathing that surrounds the electrical wiring within the cable lumen 710 of the catheter shaft 202, and thus, can extend through the cable lumen 710. The tension member 2302 can absorb tension during use, and therefore prevent damage to the electrical wiring when stress is applied to the catheter.

In an embodiment, the tension member 2302 can be secured within the lumen hub 306. For example, the tension member 2302 can wrap around one or more of the posts 1012 of the hub shell 904. The Kevlar cable can be wrapped around the posts 1012 in a figure-eight configuration, by way of example. Anchoring the tension member 2302 around the posts 1012 of the hub shell 904 can secure the tension member 2302 and allow the tension member 2302 to perform the function of absorbing strain applied to the catheter.

Figure 24:
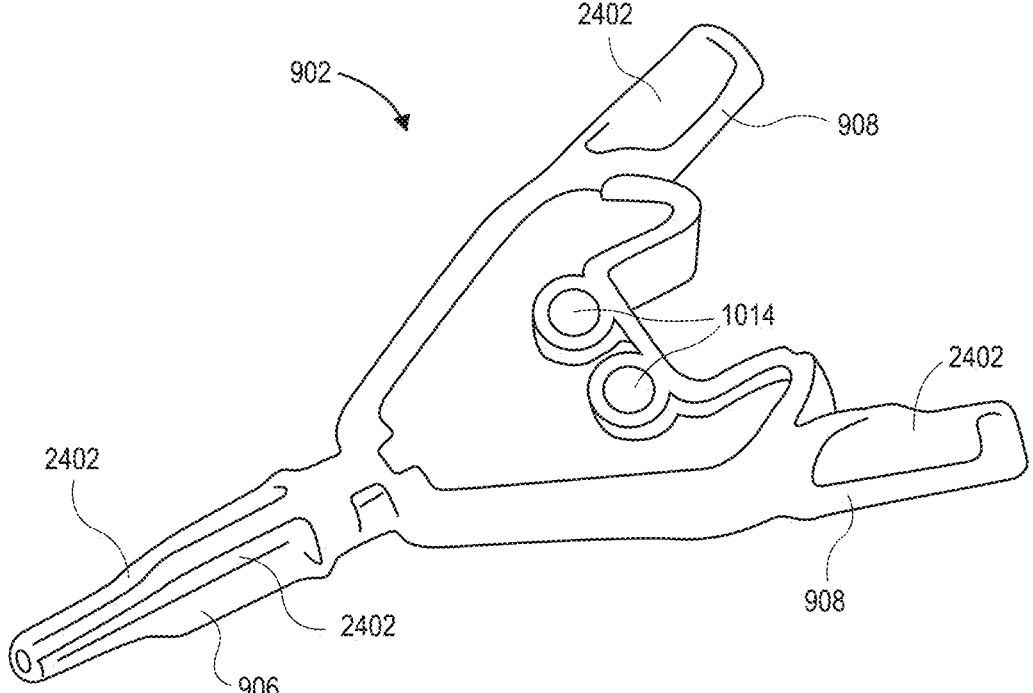
FIG. 24 is a perspective view of an innermold of a tissue treatment catheter, in accordance with an embodiment.

Referring to FIG. 24, a perspective view of an innermold of a tissue treatment catheter is shown in accordance with an embodiment. The innermold 902 can have features similar to those described above with respect to FIG. 10. For example, the innermold 902 can include a distal strain relief 906, proximal strain reliefs 908, post holes 1014, etc. In an embodiment, the strain reliefs of the innermold 902 can be shelled out to improve manufacturability. For example, rather than having cylindrical outer surfaces as shown in FIG. 10, the strain reliefs may have one or more flat surfaces 2402. The flat surfaces 2402 can result from minimizing material in the strain reliefs such that a wall thickness of the strain reliefs is more consistent throughout the strain relief structures. For example, wall thickness of the strain relief at any point along the structures can be within 10% of wall thicknesses at other locations of the innermold 902. The consistent wall thicknesses can ensure that mold filling and cooling occurs consistently and, thus, can improve manufacturing yields.

EXAMPLE SYSTEMS AND METHODS

Example 1. A tissue treatment catheter, comprising: a catheter shaft having a distal shaft end, a fluid lumen, a guidewire port, and a guidewire lumen, wherein the guidewire lumen extends from the distal shaft end to the guidewire port; a balloon mounted on the catheter shaft and having an interior in fluid communication with the fluid lumen; an ultrasound transducer located in the interior and having a transducer lumen; and an isolation tube extending through the transducer lumen and the guidewire lumen to a proximal tube end between the distal shaft end and the guidewire port.

Example 2. The catheter of example 1, wherein the guidewire port extends through a sidewall of the catheter shaft into the guidewire lumen, and wherein the proximal tube end is disposed closer to the guidewire port than the distal shaft end.

Example 3. The catheter of example 2, wherein the proximal tube end is disposed at the guidewire port.

Example 4. The catheter of example 1 further comprising a stabilizing member extending through the guidewire lumen proximal to the isolation tube.

Example 5. The catheter of example 4, wherein the stabilizing member includes a flat distal portion and a round proximal portion.

Example 6. The catheter of example 1, wherein the catheter shaft includes a cable lumen, and further comprising an electrical cable extending through the cable lumen to deliver energy to the ultrasound transducer.

Example 7. A tissue treatment catheter, comprising: a catheter shaft having a central axis, a fluid lumen, and a guidewire lumen, wherein the guidewire lumen has a lumen axis radially offset from the central axis; a balloon mounted on the catheter shaft and having an interior in fluid communication with the fluid lumen; an ultrasound transducer disposed in the interior and having a transducer lumen, wherein the central axis extends through the transducer lumen; and an isolation tube extending through the transducer lumen along the central axis and through the guidewire lumen along the lumen axis.

Example 8. The catheter of example 7, wherein the transducer lumen is centered on the central axis.

Example 9. The catheter of example 7, wherein a transducer axis of the transducer lumen is closer to the central axis than the lumen axis.

Example 10. The catheter of example 7, wherein a transducer axis of the transducer lumen is coaxially aligned with the central axis.

Example 11. The catheter of example 7, wherein the isolation tube includes a jog.

Example 12. The catheter of example 11, wherein the jog is longitudinally between the ultrasound transducer and the catheter shaft.

Example 13. The catheter of example 11, wherein the isolation tube includes a distal tube axis distal to the jog and a proximal tube axis proximal to the jog, wherein the distal tube axis is not coaxial with the proximal tube axis, and wherein the proximal tube axis is coaxial with the lumen axis.

Example 14. The catheter of example 13, wherein the distal tube axis is closer to a transducer axis of the transducer lumen or the central axis of the catheter shaft than the lumen axis, and wherein the proximal tube axis is closer to the lumen axis than the transducer axis or the central axis.

Example 15. The catheter of example 11, wherein the catheter shaft includes a notch at a distal catheter end, and wherein the jog is received within the notch.

Example 16. The catheter of example 15 further comprising an adhesive joint between the jog and the distal catheter end.

Example 17. The catheter of example 7, wherein the catheter shaft includes a cable lumen, and further comprising an electrical cable extending through the cable lumen to deliver energy to the ultrasound transducer.

Example 18. The catheter of example 7, wherein the isolation tube includes a core tube having a tie layer.

Example 19. The catheter of example 18, wherein the core tube is formed from polyimide, and wherein the tie layer includes a urethane coating layer.

Example 20. The catheter of example 18, wherein the tie layer has a thickness in a range of 5-15 microns.

Example 21. A tissue treatment catheter, comprising: a catheter shaft having a first fluid lumen, a second fluid lumen, and a cable lumen; a balloon mounted on the catheter shaft and having an interior in fluid communication with the first fluid lumen and the second fluid lumen; an ultrasound transducer in the interior; a lumen hub coupled to the catheter shaft and including a first fluid tube in fluid communication with the first fluid lumen and a second fluid tube in fluid communication with the second fluid lumen, wherein the first fluid tube and the second fluid tube extend outward from a longitudinal axis of the catheter shaft in a wye configuration; and an electrical connector coupled to the lumen hub radially between the first fluid tube and the second fluid tube.

Example 22. The catheter of example 21, wherein the lumen hub includes an innermold having a distal strain relief coupled to the catheter shaft, wherein the innermold contains distal ends of the first fluid tube and the second fluid tube to place the first fluid tube and the second fluid tube in fluid communication with the first fluid lumen and the second fluid lumen, and wherein the innermold has a central cable channel in communication with the cable lumen.

Example 23. The catheter of example 22, wherein the innermold includes a proximal notch between the first fluid tube and the second fluid tube, and wherein the lumen hub includes a hub shell surrounding the innermold to form a receiving cavity within the proximal notch.

Example 24. The catheter of example 23 further comprising an extension cable extending from the electrical connector, wherein the extension cable includes a connector housing mounted within the receiving cavity.

Example 25. The catheter of example 24, wherein the extension cable is longer than the first fluid tube and the second fluid tube.

Example 26. The catheter of example 24, wherein the extension cable includes a mending board within the connector housing, wherein the mending board includes a distal electrical contact on a substrate, and a proximal electrical contact on the substrate, wherein an electrical cable extends from the distal electrical contact through the cable lumen, and wherein an extension cable wire extends from the proximal electrical contact to a proximal connector of the extension cable.

Example 27. The catheter of example 24, wherein one or more of the innermold or the hub shell includes a slot, and wherein a key of the connector housing is located in the slot.

Example 28. The catheter of example 21 further comprising a tension member extending through the cable lumen, wherein the tension member is wrapped around a post of a hub shell.

Example 29. A method, comprising: inserting an isolation tube of a distal catheter subassembly into a guidewire lumen of a catheter shaft of a medial catheter subassembly, wherein the distal catheter subassembly includes an ultrasound transducer mounted on the isolation tube and a balloon containing the ultrasound transducer, and wherein the catheter shaft includes a first fluid lumen and a second fluid lumen in fluid communication with an interior of the balloon; and bonding an electrical cable of the medial catheter subassembly to a mending board of a proximal catheter subassembly, wherein the proximal catheter subassembly includes a connector housing containing the mending board, and an extension cable wire extending proximally from the mending board to a proximal connector.

Example 30. The method of example 29 further comprising attaching the isolation tube to the catheter shaft.

Example 31. The method of example 29 further comprising locating a key of the connector housing in a slot of a lumen hub of the proximal catheter subassembly.

Example 32. A method, comprising: inserting a shaping mandrel into an isolation tube lumen of an isolation tube, wherein the shaping mandrel includes a mandrel jog, and wherein the isolation tube includes a core tube having a tie layer; heat setting the isolation tube such that the jog is set in one or more of the core tube or the tie layer; and inserting the isolation tube into a guidewire lumen of a catheter shaft.

Example 33. The method of example 32, wherein the core tube is formed from polyimide, and wherein the tie layer includes a urethane coating layer.

Example 34. The method of example 32, wherein the tie layer has a thickness in a range of 5-15 microns.

Example 35. A tissue treatment catheter, comprising: a catheter shaft having a distal shaft end, a guidewire port, and a guidewire lumen, wherein the guidewire lumen extends from the distal shaft end to the guidewire port; a transducer having a transducer lumen; and an isolation tube extending through the transducer lumen and the guidewire lumen to the guidewire port, wherein the isolation tube includes a jog, and wherein the jog is longitudinally between the transducer and the catheter shaft.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A tissue treatment catheter, comprising:
a catheter shaft having a distal shaft end, a fluid lumen, a guidewire port, and a guidewire lumen, wherein the guidewire lumen extends from the distal shaft end to the guidewire port;
a balloon mounted on the catheter shaft and having an interior in fluid communication with the fluid lumen;
an ultrasound transducer located in the interior and having a transducer lumen; and
an isolation tube extending through the transducer lumen and into the guidewire lumen to terminate at a proximal tube end between the distal shaft end and the guidewire port.

2. The tissue treatment catheter of claim 1, wherein the guidewire port extends through a sidewall of the catheter shaft into the guidewire lumen, and wherein the proximal tube end is disposed closer to the guidewire port than the distal shaft end.

3. The tissue treatment catheter of claim 2, wherein the proximal tube end is disposed at the guidewire port.

4. The tissue treatment catheter of claim 1 further comprising a stabilizing member extending through the guidewire lumen proximal to the isolation tube.

5. The tissue treatment catheter of claim 4, wherein the stabilizing member includes a flat distal portion and a round proximal portion.

6. The tissue treatment catheter of claim 1, wherein the catheter shaft includes a cable lumen, and further comprising an electrical cable extending through the cable lumen to deliver energy to the ultrasound transducer.

7. A tissue treatment catheter, comprising:
a catheter shaft having a central axis, a fluid lumen, and a guidewire lumen, wherein the guidewire lumen has a lumen axis radially offset from the central axis;
a balloon mounted on the catheter shaft and having an interior in fluid communication with the fluid lumen;
an ultrasound transducer disposed in the interior and having a transducer axis coaxially aligned with the central axis, wherein the central axis extends through a transducer lumen of the transducer; and
an isolation tube extending through the transducer lumen along the transducer axis and bends into and through the guidewire lumen along the lumen axis radially offset from the transducer axis.

8. The tissue treatment catheter of claim 7, wherein the transducer lumen is centered on the central axis.

9. The tissue treatment catheter of claim 7, wherein a transducer axis of the transducer lumen is closer to the central axis than the lumen axis.

10. The tissue treatment catheter of claim 7, wherein a transducer axis of the transducer lumen is coaxially aligned with the central axis.

11. The tissue treatment catheter of claim 7, wherein the isolation tube includes a jog.

12. The tissue treatment catheter of claim 11, wherein the jog is longitudinally between the ultrasound transducer and the catheter shaft.

13. The tissue treatment catheter of claim 11, wherein the isolation tube includes a distal tube axis distal to the jog and a proximal tube axis proximal to the jog, wherein the distal tube axis is not coaxial with the proximal tube axis, and wherein the proximal tube axis is coaxial with the lumen axis.

14. The tissue treatment catheter of claim 13, wherein the distal tube axis is closer to a transducer axis of the transducer lumen or the central axis of the catheter shaft than the lumen axis, and wherein the proximal tube axis is closer to the lumen axis than the transducer axis or the central axis.

15. The tissue treatment catheter of claim 11, wherein the catheter shaft includes a notch at a distal catheter end, and wherein the jog is received within the notch.

16. The tissue treatment catheter of claim 15 further comprising an adhesive joint between the jog and the distal catheter end.

17. The tissue treatment catheter of claim 7, wherein the catheter shaft includes a cable lumen, and further comprising an electrical cable extending through the cable lumen to deliver energy to the ultrasound transducer.

18. The tissue treatment catheter of claim 7, wherein the isolation tube includes a core tube having a tie layer.

19. The tissue treatment catheter of claim 18, wherein the core tube is formed from polyimide, and wherein the tie layer includes a urethane coating layer.

20. The tissue treatment catheter of claim 18, wherein the tie layer has a thickness in a range of 5-15 microns.

21. A tissue treatment catheter, comprising:
a catheter shaft having a first fluid lumen, a second fluid lumen, and a cable lumen;
a balloon mounted on the catheter shaft and having an interior in fluid communication with the first fluid lumen and the second fluid lumen;
an ultrasound transducer in the interior;
a lumen hub coupled to the catheter shaft and including a first fluid tube in fluid communication with the first fluid lumen and a second fluid tube in fluid communication with the second fluid lumen, wherein the first fluid tube and the second fluid tube extend outward from a longitudinal axis of the catheter shaft in a wye configuration, and wherein the lumen hub includes an innermold having a proximal notch between the wye configuration of the first fluid tube and the second fluid tube; and an electrical connector coupled to the lumen hub radially between the first fluid tube and the second fluid tube.

22. The tissue treatment catheter of claim 21, wherein the innermold has a distal strain relief coupled to the catheter shaft, wherein the innermold contains distal ends of the first fluid tube and the second fluid tube to place the first fluid tube and the second fluid tube in fluid communication with the first fluid lumen and the second fluid lumen, and wherein the innermold has a central cable channel in communication with the cable lumen.

23. The tissue treatment catheter of claim 22, wherein the lumen hub includes a hub shell surrounding the innermold to form a receiving cavity within the proximal notch.

24. The tissue treatment catheter of claim 23 further comprising an extension cable extending from the electrical connector, wherein the extension cable includes a connector housing mounted within the receiving cavity.

25. The tissue treatment catheter of claim 24, wherein the extension cable is longer than the first fluid tube and the second fluid tube.

26. The tissue treatment catheter of claim 24, wherein the extension cable includes a mending board within the connector housing, wherein the mending board includes a distal electrical contact on a substrate, and a proximal electrical contact on the substrate, wherein an electrical cable extends from the distal electrical contact through the cable lumen, and wherein an extension cable wire extends from the proximal electrical contact to a proximal connector of the extension cable.

27. The tissue treatment catheter of claim 24, wherein one or more of the innermold or the hub shell includes a slot, and wherein a key of the connector housing is located in the slot.

28. The tissue treatment catheter of claim 21 further comprising a tension member extending through the cable lumen, wherein the tension member is wrapped around a post of a hub shell.

29. A tissue treatment catheter, comprising:

a catheter shaft having a distal shaft end, a guidewire port, and a guidewire lumen, wherein the guidewire lumen extends from the distal shaft end to the guidewire port;

a transducer having a transducer lumen; and an isolation tube extending through the transducer lumen and the guidewire lumen to the guidewire port, wherein the isolation tube includes a jog, and wherein the jog is longitudinally between the transducer and the catheter shaft.

\* \* \* \* \*